United States Patent
O'Malley et al.

(10) Patent No.: US 10,082,510 B2
(45) Date of Patent: Sep. 25, 2018

(54) SRC-2 USE AS METABOLIC BIOMARKER FOR DIAGNOSIS AND TREATMENT OF METASTATIC PROSTATE CANCER

(71) Applicant: Baylor College of Medicine, Houston, TX (US)

(72) Inventors: Bert W. O'Malley, Houston, TX (US); Subhamoy Dasgupta, Houston, TX (US); Nicholas Mitsiades, Boston, MA (US); Arun Sreekumar, Sugar Land, TX (US); Sean E. Mcguire, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 15/309,143

(22) PCT Filed: May 5, 2015

(86) PCT No.: PCT/US2015/029307
§ 371 (c)(1),
(2) Date: Nov. 4, 2016

(87) PCT Pub. No.: WO2015/171652
PCT Pub. Date: Nov. 12, 2015

(65) Prior Publication Data
US 2017/0067903 A1 Mar. 9, 2017

Related U.S. Application Data

(60) Provisional application No. 62/109,762, filed on Jan. 30, 2015, provisional application No. 61/988,381, filed on May 5, 2014.

(51) Int. Cl.
| | |
|---|---|
| *G01N 33/60* | (2006.01) |
| *G01N 33/00* | (2006.01) |
| *G01N 33/48* | (2006.01) |
| *G01N 33/574* | (2006.01) |
| *A61K 31/585* | (2006.01) |
| *A61K 38/24* | (2006.01) |
| *C12Q 1/16* | (2006.01) |
| *G21H 5/02* | (2006.01) |
| *A61K 31/198* | (2006.01) |

(52) U.S. Cl.
CPC .......... *G01N 33/60* (2013.01); *A61K 31/198* (2013.01); *A61K 31/585* (2013.01); *A61K 38/24* (2013.01); *C12Q 1/16* (2013.01); *G01N 33/00* (2013.01); *G01N 33/48* (2013.01); *G01N 33/574* (2013.01); *G01N 33/57434* (2013.01); *G21H 5/02* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

WO  2012149245 A2  11/2012

OTHER PUBLICATIONS

Mullen et al., "Reductive carboxylation supports growth in tumour cells with defective mitochondria", Nature, Nov. 20, 2011, vol. 481, pp. 385-388.

Dasgupta et al. "Steroid receptor coactivator-2 mediates oncogenic reprogramming of cancer cell metabolism", Cancer Res 72, Apr. 15, 2012.

Dasgupta et al., "Coactivator SRC-2-dependent metabolic reprogramming mediates prostate cancer survival and metastasis", The Journal of clinical investigation 125.125 (3) (Mar. 2015): 1174-1188.

*Primary Examiner* — Elly-Gerald Stoica
(74) *Attorney, Agent, or Firm* — Norton Rose Fulbright US LLP

(57) ABSTRACT

Embodiments of the disclosure include methods and compositions for treatment of prostate cancer, including metastatic prostate cancer or prostate cancer at risk for developing into metastatic prostate cancer, by providing an effective therapy to an individual that has been determined to have elevated levels of SRC-2 (also known as NCOA2, GRIP1 TIF2). In particular cases, sample from an individual known to have prostate cancer is assayed for the risk for developing metastatic prostate cancer and the individual is provided an effective therapy upon determination of elevated levels of SRC-2.

13 Claims, 22 Drawing Sheets

|  |  | Fold Change (comparing to siGFP-Control) | | | |
|---|---|---|---|---|---|
|  |  | siRNA-SRC-2 | | | |
|  |  | Fold Change | 95% CI | Comments | Fold Regulation |
| A01 | SRC1 | 1.2544 | ( 1.16, 1.34 ) | OKAY | 1.2544 |
| A02 | SRC2 | 0.2331 | ( 0.21, 0.25 ) | OKAY | -4.2894 |
| A03 | SRC3 | 1.3666 | ( 1.25, 1.48 ) | OKAY | 1.3666 |
| A04 | CS | 1.2065 | ( 1.09, 1.33 ) | OKAY | 1.2065 |
| A05 | IDH1 | 0.8113 | ( 0.74, 0.88 ) | OKAY | -1.2325 |
| A06 | ACTB | 0.9251 | ( 0.85, 1.00 ) | OKAY | -1.0809 |
| A07 | GAPDH | 0.9344 | ( 0.84, 1.02 ) | OKAY | -1.0702 |
| A08 | IDH2 | 0.8208 | ( 0.75, 0.89 ) | OKAY | -1.2183 |
| A09 | IDH3A | 1.2761 | ( 1.19, 1.36 ) | OKAY | 1.2761 |
| A10 | IDH3B | 1.2227 | ( 1.13, 1.32 ) | OKAY | 1.2227 |
| A11 | IDH3G | 1.0023 | ( 0.94, 1.07 ) | OKAY | 1.0023 |
| A12 | ACO1 | 1.2026 | ( 1.11, 1.29 ) | OKAY | 1.2026 |
| B1 | ACO2 | 0.914 | ( 0.86, 0.97 ) | OKAY | -1.0941 |
| B2 | SDHA | 0.7583 | ( 0.71, 0.81 ) | OKAY | -1.3188 |
| B3 | SDHB | 1.1257 | ( 1.06, 1.20 ) | OKAY | 1.1257 |
| B4 | ELOVL5 | 1.0801 | ( 1.04, 1.12 ) | OKAY | 1.0801 |
| B5 | ACOT1 | 1.0399 | ( 0.97, 1.11 ) | OKAY | 1.0399 |
| B6 | ELOVL1 | 1.1637 | ( 1.06, 1.27 ) | OKAY | 1.1637 |
| B7 | ELOVL3 | 1.1467 | ( 1.03, 1.27 ) | B | 1.1467 |
| B8 | ELOVL4 | 1.9534 | ( 1.79, 2.11 ) | OKAY | 1.9534 |
| B9 | ELOVL6 | 1.5785 | ( 1.54, 1.62 ) | OKAY | 1.5785 |
| B10 | ELOVL7 | 1.9403 | ( 1.78, 2.10 ) | A | 1.9403 |
| B11 | ACLY | 1.3521 | ( 1.31, 1.40 ) | OKAY | 1.3521 |
| B12 | ACACA | 1.0014 | ( 0.90, 1.10 ) | OKAY | 1.0014 |
| C1 | HMGCR | 1.1344 | ( 1.08, 1.19 ) | OKAY | 1.1344 |
| C2 | LPIN | 1.466 | ( 1.29, 1.64 ) | OKAY | 1.466 |
| C3 | FASN | 0.3788 | ( 0.29, 0.47 ) | OKAY | -2.6396 |
| C4 | SCD | 0.332 | ( 0.32, 0.34 ) | OKAY | -3.0121 |
| C5 | HCS1 | 1.9319 | ( 1.83, 2.04 ) | OKAY | 1.9319 |
| C6 | HCS2 | 0.5156 | ( 0.47, 0.57 ) | OKAY | -1.9396 |
| C7 | ACTB | 1.0922 | ( 1.01, 1.17 ) | OKAY | 1.0922 |
| C8 | GAPDH | 1.0212 | ( 1.00, 1.04 ) | OKAY | 1.0212 |
| C9 | GNS | 1.332 | ( 1.29, 1.38 ) | OKAY | 1.332 |
| C10 | GFPT1 | 1.3493 | ( 1.28, 1.42 ) | OKAY | 1.3493 |
| C11 | UGDH | 1.4545 | ( 1.40, 1.51 ) | OKAY | 1.4545 |
| C12 | FH | 1.0829 | ( 1.05, 1.11 ) | OKAY | 1.0829 |
| D1 | GLUD1 | 1.0061 | ( 1.00, 1.01 ) | OKAY | 1.0061 |
| D2 | GLUD2 | 1.1698 | ( 1.15, 1.19 ) | OKAY | 1.1698 |
| D3 | GLS | 0.9269 | ( 0.89, 0.96 ) | OKAY | -1.0788 |
| D4 | GLS2 | 0.8775 | ( 0.82, 0.94 ) | OKAY | -1.1396 |
| D5 | ACTB | 1.1303 | ( 1.12, 1.14 ) | OKAY | 1.1303 |
| D6 | GAPDH | 0.953 | ( 0.92, 0.98 ) | OKAY | -1.0493 |
| D7 | PRPS1 | 1.4922 | ( 1.47, 1.51 ) | OKAY | 1.4922 |
| D8 | PRPS2 | 1.183 | ( 1.12, 1.24 ) | OKAY | 1.183 |
| D9 | G6PD | 1.2178 | ( 1.15, 1.29 ) | OKAY | 1.2178 |
| D10 | PGLS | 0.836 | ( 0.78, 0.89 ) | OKAY | -1.1961 |
| D11 | PGD | 1.2016 | ( 1.14, 1.26 ) | OKAY | 1.2016 |
| D12 | RBKS | 1.2803 | ( 1.16, 1.40 ) | OKAY | 1.2803 |

FIG. 18

| E1 | RGN | 1.3329 | (1.22, 1.44) | C | 1.3329 |
|---|---|---|---|---|---|
| E2 | MCATa | 1.1351 | (1.11, 1.16) | OKAY | 1.1351 |
| E3 | MCATb | 1.326 | (1.21, 1.44) | OKAY | 1.326 |
| E4 | ACACB | 1.0898 | (1.00, 1.18) | OKAY | 1.0898 |
| E5 | OXSM | 0.9587 | (0.87, 1.04) | OKAY | -1.0431 |
| E6 | OLAH | 3.0405 | (2.92, 3.16) | OKAY | 3.0405 |
| E7 | ACAA2 | 1.0987 | (0.99, 1.20) | OKAY | 1.0987 |
| E8 | ACOT2 | 0.9204 | (0.91, 0.94) | A | -1.0865 |
| E9 | ACOT7 | 1.3237 | (1.02, 1.63) | B | 1.3237 |
| E10 | ELOVL2 | 1.4038 | (1.34, 1.46) | OKAY | 1.4038 |
| E11 | ACTB | 1.1039 | (1.01, 1.20) | OKAY | 1.1039 |
| E12 | GAPDH | 0.8722 | (0.81, 0.93) | OKAY | -1.1465 |
| F1 | PDHA1 | 1.1894 | (1.02, 1.36) | OKAY | 1.1894 |
| F2 | PDHA2 | 4.0942 | (3.72, 4.47) | OKAY | 4.0942 |
| F3 | PDHB | 1.1421 | (1.05, 1.23) | OKAY | 1.1421 |
| F4 | PDK1 | 0.9349 | (0.85, 1.02) | OKAY | -1.0696 |
| F5 | PDK2 | 1.016 | (0.93, 1.11) | OKAY | 1.016 |
| F6 | PDK3 | 0.6782 | (0.62, 0.74) | OKAY | -1.4745 |
| F7 | PDK4 | 0.719 | (0.65, 0.79) | OKAY | -1.3908 |
| F8 | SDHC | 0.877 | (0.79, 0.96) | OKAY | -1.1402 |
| F9 | SDHD | 1.0713 | (1.00, 1.14) | OKAY | 1.0713 |
| F10 | ACAA1 | 1.2875 | (1.18, 1.40) | OKAY | 1.2875 |
| F11 | ACAA2 | 0.8794 | (0.81, 0.95) | OKAY | -1.1371 |
| F12 | ACAD10 | 0.7045 | (0.65, 0.76) | OKAY | -1.4195 |
| G01 | ACAD11 | 1.4892 | (1.36, 1.61) | OKAY | 1.4892 |
| G02 | ACAD9 | 1.0386 | (0.95, 1.13) | OKAY | 1.0386 |
| G03 | ACADL | 3.3743 | (3.09, 3.66) | OKAY | 3.3743 |
| G04 | ACADM | 0.6665 | (0.61, 0.72) | OKAY | -1.5005 |
| G05 | ACADS | 0.8613 | (0.79, 0.93) | A | -1.161 |
| G06 | ACADSB | 0.6573 | (0.60, 0.71) | A | -1.5214 |
| G07 | ACADVL | 1.0752 | (0.98, 1.17) | OKAY | 1.0752 |
| G08 | ACAT1 | 1.7346 | (1.59, 1.88) | OKAY | 1.7346 |
| G09 | ACAT2 | 0.6852 | (0.63, 0.74) | OKAY | -1.4594 |
| G10 | ACOT1 | 1.3329 | (1.22, 1.44) | C | 1.3329 |
| G11 | ACOT12 | 1.3329 | (1.22, 1.44) | C | 1.3329 |
| G12 | ACOT2 | 0.8673 | (0.79, 0.94) | OKAY | -1.153 |
| H01 | ACOT6 | 1.2523 | (1.15, 1.36) | OKAY | 1.2523 |
| H02 | ACOT7 | 0.969 | (0.89, 1.05) | OKAY | -1.032 |
| H03 | ACOT8 | 0.4489 | (0.41, 0.49) | OKAY | -2.2275 |
| H04 | ACOT9 | 1.3704 | (1.26, 1.49) | OKAY | 1.3704 |
| H05 | ACOX1 | 0.7871 | (0.72, 0.85) | OKAY | -1.2705 |
| H06 | ACOX2 | 0.5086 | (0.47, 0.55) | OKAY | -1.9662 |
| H07 | ACOX3 | 0.8979 | (0.82, 0.97) | OKAY | -1.1137 |
| H08 | ACSBG1 | 1.3515 | (1.24, 1.47) | OKAY | 1.3515 |
| H09 | ACSBG2 | 0.7094 | (0.65, 0.77) | A | -1.4097 |
| H10 | ACSL1 | 1.4996 | (1.37, 1.63) | OKAY | 1.4996 |
| H11 | ACSL3 | 0.5883 | (0.54, 0.64) | OKAY | -1.6999 |
| H12 | ACSL4 | 1.1054 | (1.01, 1.20) | OKAY | 1.1054 |
| I1 | ACSL5 | 2.1804 | (2.00, 2.36) | OKAY | 2.1804 |
| I2 | ACSL6 | 0.9231 | (0.85, 1.00) | B | -1.0833 |
| I3 | ACSM2A | 1.3329 | (1.22, 1.44) | C | 1.3329 |
| I4 | ACSM3 | 0.8494 | (0.78, 0.92) | OKAY | -1.1772 |

FIG. 18 (CONT'D)

| | | | | | |
|---|---|---|---|---|---|
| I5 | ACSM4 | 1.3329 | (1.22, 1.44) | C | 1.3329 |
| I6 | ACSM5 | 1.3329 | (1.22, 1.44) | C | 1.3329 |
| I7 | ALDH2 | 1.0314 | (0.94, 1.12) | B | 1.0314 |
| I8 | BDH1 | 1.3515 | (1.24, 1.47) | OKAY | 1.3515 |
| I9 | BDH2 | 0.6852 | (0.63, 0.74) | OKAY | -1.4594 |
| I10 | CPT1A | 1.2965 | (1.19, 1.41) | OKAY | 1.2965 |
| I11 | CPT1B | 0.9623 | (0.88, 1.04) | OKAY | -1.0392 |
| I12 | CPT1C | 0.9041 | (0.83, 0.98) | OKAY | -1.1061 |
| J1 | CPT2 | 1.5205 | (1.39, 1.65) | OKAY | 1.5205 |
| J2 | CRAT | 1.2181 | (1.12, 1.32) | OKAY | 1.2181 |
| J3 | CROT | 0.5193 | (0.48, 0.56) | OKAY | -1.9257 |
| J4 | DECR1 | 1.0243 | (0.94, 1.11) | OKAY | 1.0243 |
| J5 | DECR2 | 1.3704 | (1.26, 1.49) | OKAY | 1.3704 |
| J6 | ECHS1 | 0.6948 | (0.64, 0.75) | OKAY | -1.4394 |
| J7 | EHHADH | 0.8205 | (0.75, 0.89) | OKAY | -1.2188 |
| J8 | FABP1 | 1.3329 | (1.22, 1.44) | C | 1.3329 |
| J9 | FABP2 | 1.2965 | (1.19, 1.41) | OKAY | 1.2965 |
| J10 | FABP3 | 1.1766 | (1.08, 1.28) | OKAY | 1.1766 |
| J11 | FABP4 | 0.6852 | (0.63, 0.74) | OKAY | -1.4594 |
| J12 | FABP5 | 1.2523 | (1.15, 1.36) | OKAY | 1.2523 |
| K1 | FABP6 | 3.903 | (3.57, 4.23) | A | 3.903 |
| K2 | GCDH | 1.1684 | (1.07, 1.27) | OKAY | 1.1684 |
| K3 | GK | 0.4981 | (0.46, 0.54) | OKAY | -2.0075 |
| K4 | GK2 | 1.3329 | (1.22, 1.44) | C | 1.3329 |
| K5 | GPD1 | 1.2965 | (1.19, 1.41) | OKAY | 1.2965 |
| K6 | GPD2 | 0.6349 | (0.58, 0.69) | OKAY | -1.5751 |
| K7 | HADHA | 0.936 | (0.86, 1.01) | OKAY | -1.0684 |
| K8 | HMGCL | 1.0678 | (0.98, 1.16) | OKAY | 1.0678 |
| K9 | HMGCS1 | 1.0386 | (0.95, 1.13) | OKAY | 1.0386 |
| K10 | HMGCS2 | 1.1286 | (1.03, 1.22) | B | 1.1286 |
| K11 | LIPE | 0.9557 | (0.88, 1.04) | B | -1.0464 |
| K12 | LPL | 1.3329 | (1.22, 1.44) | C | 1.3329 |
| L1 | MCEE | 2.2417 | (2.05, 2.43) | OKAY | 2.2417 |
| L2 | MUT | 1.1054 | (1.01, 1.20) | OKAY | 1.1054 |
| L3 | OXCT2 | 0.5413 | (0.50, 0.59) | OKAY | -1.8473 |
| L4 | ECI2 | 0.7709 | (0.71, 0.84) | OKAY | -1.2972 |
| L5 | PECR | 1.3237 | (1.21, 1.43) | OKAY | 1.3237 |
| L6 | PPA1 | 0.9104 | (0.83, 0.99) | OKAY | -1.0984 |
| L7 | PRKAA1 | 1.2965 | (1.19, 1.41) | OKAY | 1.2965 |
| L8 | PRKAA2 | 1.5851 | (1.45, 1.72) | OKAY | 1.5851 |
| L9 | PRKAB1 | 0.7603 | (0.70, 0.82) | OKAY | -1.3153 |
| L10 | PRKAB2 | 1.4385 | (1.32, 1.56) | OKAY | 1.4385 |
| L11 | PRKACA | 1.0172 | (0.93, 1.10) | OKAY | 1.0172 |
| L12 | PRKACB | 0.6175 | (0.57, 0.67) | OKAY | -1.6194 |
| M1 | PRKAG1 | 1.641 | (1.50, 1.78) | OKAY | 1.641 |
| M2 | PRKAG2 | 1.3237 | (1.21, 1.43) | OKAY | 1.3237 |
| M3 | PRKAG3 | 0.9894 | (0.91, 1.07) | B | -1.0107 |
| M4 | SLC27A1 | 0.832 | (0.76, 0.90) | A | -1.202 |
| M5 | SLC27A2 | 1.4385 | (1.32, 1.56) | OKAY | 1.4385 |
| M6 | SLC27A3 | 0.5265 | (0.48, 0.57) | OKAY | -1.8992 |
| M7 | SLC27A4 | 1.2965 | (1.19, 1.41) | OKAY | 1.2965 |
| M8 | SLC27A5 | 1.6184 | (1.48, 1.75) | OKAY | 1.6184 |

FIG. 18 (CONT'D)

| M9 | SLC27A6 | 0.3045 | ( 0.28, 0.33 ) | OKAY | -3.2839 |
|----|---------|--------|----------------|------|---------|
| | | | | | |
| | | | | | |

Comments:

A: This gene's average threshold cycle is relatively high (> 30) in either the control or the test sample, and is reasonably low in the other sample (< 30).

These data mean that the gene's expression is relatively low in one sample and reasonably detected in the other sample suggesting that the actual fold-change value is at least as large as the calculated and reported fold-change result.

This fold-change result may also have greater variations if p value > 0.05; therefore, it is important to have a sufficient number of biological replicates to validate the result for this gene.

B: This gene's average threshold cycle is relatively high (> 30), meaning that its relative expression level is low, in both control and test samples, and the p-value for the fold-change is either unavailable or relatively high (p > 0.05).

This fold-change result may also have greater variations; therefore, it is important to have a sufficient number of biological replicates to validate the result for this gene.

C: This gene's average threshold cycle is either not determined or greater than the defined cut-off value (default 35), in both samples meaning that its expression was undetected, making this fold-change result erroneous and un-interpretable.

Fold Change & Fold Regulation:

Fold-Change ($2^{\wedge}$(- Delta Delta Ct)) is the normalized gene expression ($2^{\wedge}$(- Delta Ct)) in the Test Sample divided the normalized gene expression ($2^{\wedge}$(- Delta Ct)) in the Control Fold-Regulation represents fold-change results in a biologically meaningful way. Fold-change values greater than one indicate a positive- or an up-regulation, and the fold-regulation is equal to the fold-change.

Fold-change values less than one indicate a negative or down-regulation, and the fold-regulation is the negative inverse of the fold-change.

Fold-change and fold-regulation values greater than 2 are indicated in red; fold-change values less than 0.5 and fold-regulation values less than -2 are indicated in blue.

FIG. 18 (CONT'D)

SRC-2 USE AS METABOLIC BIOMARKER FOR DIAGNOSIS AND TREATMENT OF METASTATIC PROSTATE CANCER

This application is a national phase application under 35 U.S.C. § 371 that claims priority to International Application No. PCT/US2015/029307 filed May 5, 2015, which claims priority to U.S. Provisional Patent Application Ser. No. 61/988,381, filed May 5, 2015, and claims priority to U.S. Provisional Patent Application Ser. No. 62/109,762, filed Jan. 30, 2015, all of which are incorporated by reference herein in their entirety.

STATEMENT REGARDING FEDERALLY SPONSORED RESEARCH OR DEVELOPMENT

This invention was made with government support under Grant Number NIDDK PPG DK59820, awarded by National Institutes of Health. The government has certain rights in the invention.

TECHNICAL FIELD

The field of the disclosure includes at least the fields of biochemistry, molecular biology, cell biology, and medicine, including cancer medicine.

BACKGROUND

Tumors scavenge various nutrients for carbon and nitrogen sources required for the synthesis of biomolecules to support the growth and replication of their rapidly dividing cells. Nutrient availability plays a pivotal role in the reprogramming of tumor metabolic pathways to sustain increased energetic and anabolic demands. One of the frequent metabolic adaptations observed in different types of tumor cells is an increased uptake of glucose and aerobic glycolysis along with decreased oxidative metabolism, a phenomenon widely known as the Warburg effect (Vander Heiden, et al., 2009). However, it is well documented that tumor cells do not rely on a single metabolic-state and instead acquire a variety of strategies to adapt to alterations in nutrient availability and metabolic stress conditions during the course of disease progression (Cantor & Sabatini, 2012; Ward & Thompson, 2012). Recent studies using 13C-isotopes have identified a complimentary switch of glutamine metabolism by tumor cells to efficiently support carbon utilization for anabolism and growth (Metallo, et al., 2011; Mullen, et al., 2011). The glutamine metabolic pathway serves as a crucial source for anaplerosis of carbon atoms to balance the metabolic flux through the tricarboxylic acid cycle (TCA) cycle and to support the increased biosynthesis of macromolecules such as nucleotides and lipids, and mitochondrial ATP synthesis (Gao, et al., 2009; Wise, et al., 2008).

Unlike other solid tumors, adenocarcinoma of the prostate display very unique metabolic features since the majority of primary tumors do not show a classical 'glycolytic switch' and so are not efficiently detected in FDG-PET (Zadra, et al., 2013). Instead, an aberrant increase in de novo lipogenesis (Rossi, et al., 2003) coupled with glucose and glutamine metabolism is observed (Fendt, et al., 2013) in prostatic tumors from early clinical stages, and is significantly associated with poor prognosis and worse disease outcome (Menendez & Lupu, 2008). Lipids contribute to various aspects of tumor biology by functioning as building blocks for membrane biogenesis, phospholipids for membrane structure, lipid rafts for cell signaling, and more importantly for energy production and storage (Currie, et al., 2013). While most normal human cells prefer exogenous sources of fatty acids, tumor cells rely more on de novo fatty acid biosynthesis (Currie, et al., 2013) and this is true especially in prostate cancer cells. Thus, it is of utmost importance to identify the oncogenic factors that reprogram the metabolic pathways that maintain this increased lipogenic program in prostate tumors.

Previous findings identified steroid receptor coactivator-2 (SRC-2, also known as NCOA2, TIF2, GRIP 1), a potent transcriptional coregulator for nuclear receptors (NRs) and other transcription factors (Dasgupta, et al., 2013), as a critical coordinator of energy homeostasis (Chopra, et al., 2008; Chopra, et al., 2011; Picard, et al., 2002). Importantly, recent findings from 'integrative genomic profiling' of human prostate tumors revealed SRC-2 is a potent oncogene in ~8% of the primary tumors, but notably, in ~37% of the metastatic prostate tumors (Taylor, et al., 2010). Furthermore, prostate cancer patients harboring SRC-2 gene amplification or overexpression had higher rates of biochemical recurrence, and SRC-2 expression was a significant predictor of time-to-biochemical recurrence (Agoulnik, et al., 2006). These findings accentuate the clinical importance of the SRC-2 gene in prostate cancer pathology (Dasgupta, et al., 2012). Functionally, SRC-2 acts as a transcriptional coregulator of androgen receptor (AR) (Agoulnik, et al., 2006) in prostate cancer cells, however, its mode of action in aggressive metastatic prostate cancer (CRPC) is not clearly understood. Moreover none of the studies have yet investigated the functional role of SRC-2 in cancer metabolism, nor have they determined whether this recent but well-described association of SRC-2 is a critical requirement for prostate cancer cell survival and metastasis (Taylor, et al., 2010).

The present disclosure provides a solution to a long-felt need in the art to provide a marker for cancer metastasis.

BRIEF SUMMARY

Embodiments of the disclosure include methods of diagnosis of cancer and, in particular, a metastatic cancer. Embodiments also include methods of predicting metastasis of a cancer, including identifying whether or not an individual is at an increased risk for developing metastatic cancer, such as once a primary cancer has been identified. The methods of the disclosure allow differentiation of aggressive cancer from non-aggressive cancer, including distinguishing from indolent cancer or cancer that is localized (and, therefore, not metastatic and/or unlikely to become metastatic). Embodiments of the disclosure concern identification of oncogenic factors that reprogram the metabolic pathways that maintain an increased lipogenic program in tumors, such as prostate tumors.

Embodiments of the disclosure include a variety of methods that relate to measuring a component of a metabolic pathway that is related to tumor metastasis. In specific embodiments, the level of SRC-2 is utilized as a marker for methods related to tumor metastasis by indirectly measuring SRC-2 activity based on the levels of metabolites in a SCR-2 pathway that would not be present in normal cells or would be present at a considerably reduced level in normal cells compared to cancer cells. In specific embodiments, the metabolites in the SRC-2 pathway are identified to be present in the cancer cells or are identified to be at a level greater than would be seen in normal cells because they have a label. In specific embodiments, the label is a carbon label, including $^{13}C$.

Once an individual has been identified as having metastatic cancer or at risk for developing metastatic cancer with the analytical methods of the disclosure, the individual is provided a particular treatment. In specific embodiments, the treatment that is provided would not have been given, or would not have necessarily been given, to the individual if the analytical methods would not have been performed. In particular embodiments, a particular treatment to target SRC-2 or a metabolite in a SRC-2 pathway is provided to the individual following analytical methods of the disclosure that showed that SRC-2 expression or activity is increased (that is determined as increased by direct or indirect methods). In certain embodiments, a particular treatment that is specific for metastatic cancer is provided to the individual following identification by analytical methods of the disclosure that SRC-2 expression or activity is increased (that is determined increased by direct or indirect methods). Such treatments are employed only because the methods of the disclosure have determined that there is a specific need for them. Thus, embodiments of the disclosure allow for guidance for therapeutic decisions, wherein the guidance based on the outcome of the disclosed methods and is the direct result of that determination. Without such determination, the appropriate therapy would not or may not have been given.

Embodiments of the disclosure identify the molecular functions of SRC-2 as a transcriptional coordinator of tumor metabolism. In specific embodiments, SRC-2 dependent functions serve as molecular determinants of survival and metastases competence.

Specific embodiments of the disclosure provide evidence of an underlying metabolic coordinator facilitating growth, survival and eventually metastasis of prostate tumor cells. In particular aspects, SRC-2 expression defines a metabolically active cellular state by reprogramming cellular metabolism to utilize glutamine for fatty acid biosynthesis. In at least certain aspects, this process supplements the tumor cells with added bioenergetic and biomass proliferative advantages so that anabolic processes are not compromised. Tumor cells encounter a variety of environmental challenges during the process of metastasis, and for successful survival and growth outside the host tissue, an autonomous and highly efficient metabolic strategy providing a constant supply of energy and biosynthetic macromolecules are required. In certain embodiments, increased expression of SRC-2 in tumors reinforces these metabolic advantages which foster cell survival and homing during the metastatic spread.

In particular aspects of the disclosure, SRC-2 promotes de novo fatty acid biosynthesis in cancer cells by two distinct but inter-related processes regulating both substrate availability and rate-limiting enzymes. In specific embodiments, oncogenic functions of SRC-2 are attributed to its ability to maintain increased fatty acid biosynthesis and energy homeostasis, thereby enhancing proliferative signals for cell growth and survival by evading cell death and growth suppression checkpoints. Embodiments of the disclosure concern SRC-2-dependent metabolic reprogramming.

Embodiments of the disclosure provide for inhibition of either SRC-2 directly and/or inhibition of a metabolite in a SRC-2 pathway (including a glutamine-related metabolic pathway) to reduce tumor cell growth and metastasis. Such treatment steps stem from the determination that the levels of one or more metabolites in a SRC-2 pathway are askew in cancer cells compared to normal cells.

The monitoring of the presence of a shift from standard TCA to reductive TCA is included in aspects of the disclosure. Such monitoring occurs by monitoring the level of SRC-2, including by direct or indirect methods. In embodiments of the disclosure, elevated levels of SRC-2 enhance synthesis of fatty acids (lipids) that is essential for the survival of metastatic prostate cancer cells. In specific embodiments, SRC-2 mediates fatty acid biosynthesis by driving glutamine metabolism. The methods of the disclosure allow one to tell if reverse TCA cycle is operative, which in turn means that SRC-2 is having a major effect and driving metastasis. Thus, in specific embodiments the cancers for which such disclosed methods are informative are those that have elevated SRC-2.

In at least some embodiments, the methods of the disclosure to diagnose metastatic cancer utilizes a non-invasive method, although in some cases the method may be an invasive one, such as tissue biopsy.

Embodiments of the disclosure include mass spectrometry-based metabolic profiling, wherein the metabolic profiling indicates the level and/or activity of SRC-2 and wherein the metabolic profiling indicates a particular diagnosis and/or therapy regimen for an individual in need thereof.

In specific embodiments, methods of the disclosure include measurement of metabolic by-products and/or intermediates of SRC-2-regulated pathways from blood, prostatic fluids, or semen may be measured. Examples include citrate, isocitrate, acetyl CoA, fumarate, pyruvate, palmitic acid, stearic acid, palmitoleic acid, oleic acid, myristic acid or a combination thereof.

In embodiments of the disclosure, glutamine labeled with $^{13}C$ (all five carbons) is used as a tracer in individuals suspected of having metastatic cancer or susceptible to metastatic cancer; in certain embodiments the individual has cancer and it is desired to be determined whether or not the individual is prone to having metastatic cancer. [5-$^{13}C$]glutamine, [U-$^{13}C_5$]glutamine, L-[U-$^{13}C_5$]glutamine, $^{13}C_5$-labelled glutamine, and [U-$^{13}C$]glutamine refer to glutamine whose 5 carbon atoms are $^{13}C$ atoms, and are used interchangeably herein. In specific embodiments, glutamine is employed as a tracer because increased SRC-2 expression in metastatic tumor cells utilizes glutamine and generates citrate (with 5 out of 6 carbons labeled with $^{13}C$, referred to herein as m+5), whereas in other cells citrate with 4-carbons labeled with $^{13}C$ is produced (referred to herein as m+4). The m+5 citrate or the ratio of m+5/m+4 citrate is used to measure SRC-2 activity and metastatic potential of tumor cells, in particular embodiments. Thus, one measures citrate m+5 derived from glutamine isotopes labeled with $^{13}C$ wherein the citrate m+5 is measured by itself or in relation to another molecule, such as citrate m+4, pyruvate m+3, malate m+3 or fumarate m+3.

Thus, in certain embodiments, there is a method of treating an individual for metastatic cancer, or preventing or reducing metastatic cancer in the individual, providing a therapeutically effective amount of treatment for the cancer when a sample from the individual indicates that there is a particular level of citrate m+5 or ratio of citrate m+5/citrate m+4 that is measured by administering $^{13}C$-labeled glutamine to the individual; obtaining a sample from the individual, wherein the sample is suspected of comprising or known to comprise cancer cells; and measuring the level of citrate m+5 or the ratio of citrate m+5/citrate m+4 from the cells, wherein when the level of citrate m+5 or the ratio is elevated compared to a reference, the individual is in need of treatment, prevention, or the reduction of metastatic cancer. Also, one could measure the presence of $^{13}C$ in fatty acids, such as palmitic acid, stearic acid, palmitoleic acid, oleic acid, myristic acid (m0 to m14/m16 or m18), for example, in specific embodiments.

In other embodiments, glutamine with a single carbon atom, $C_1$, labeled with $^{13}C$ is used as a tracer in individuals suspected of having metastatic cancer or susceptible to metastatic cancer; in certain embodiments the individual has cancer and it is desired to be determined whether or not the individual is prone to having metastatic cancer. In specific embodiments, glutamine is employed as a tracer because increased SRC-2 expression in metastatic tumor cells utilizes glutamine and generates citrate (with 1 out of 6 carbons labeled with $^{13}C$, referred to herein as m+1). The m+1 citrate is used to measure SRC-2 activity and metastatic potential of tumor cells, in particular embodiments. Thus, one measures citrate m+1 derived from glutamine isotopes labeled with $^{13}C$.

In some cases, there is a method of treating an individual that is at risk for metastatic cancer, comprising the step of providing a therapeutically effective amount of treatment for the cancer when there is an elevated level of steroid receptor coactivator-2 (SRC-2) in a sample from the individual. In certain cases, there is a method of determining the risk of developing metastatic cancer in an individual, comprising the step of assaying for the level of SRC-2 (indirectly, directly, or both) in a sample from the individual.

In some embodiments, there is a method of treating an individual for metastatic cancer, or preventing or reducing metastatic cancer in the individual, comprising the step of providing a therapeutically effective amount of treatment for the cancer when a sample from the individual indicates that there is an elevated level of SRC-2 in cells from the sample, wherein the level is measured by the following: administering $^{13}C$-labeled glutamine to the individual; obtaining a sample from the individual, wherein the sample is suspected of comprising or known to comprise cancer cells; and measuring the level of citrate m+5, citrate m+1, or the ratio of citrate m+5/citrate m+4 from the cells, wherein when the level of citrate m+5, citrate m+1, or the ratio is elevated compared to a reference, the individual is in need of treatment, prevention, or the reduction of metastatic cancer. In specific embodiments, the cancer is of the prostate, breast, lung, liver, ovarian, endometrial, or colon. In some cases, the sample is urine, serum, blood, tissue biopsy, prostatic fluid, semen, breath, secretions, or a mixture thereof. In specific embodiments, the treatment comprises one or more agents that inhibit the level and/or activity of SRC-2, such as one or more functionally active derivatives of bufalin (wherein a functionally active derivative of bufalin is defined as a derivative that inhibits the level and/or activity of SRC-2). In particular embodiments, the level and/or activity of SRC-2 is inhibited by nucleic acid targeting of SRC-2 mRNA. In specific cases, the treatment comprises chemotherapy, hormone therapy, immunotherapy, radiation, surgery, or a combination thereof. Some embodiments provide for further comprising the step of administering one or more glutamine analogs to the individual, such as one or more glutamine analogs is selected from the group consisting of 6-diazo-5-oxo-L-norleucine (DON), L-g-glutamyl-p-nitroanilide (GPNA), and a mixture thereof.

In some cases, a treatment for prostate cancer, including metastatic prostate cancer, includes a LHRH analog, antiandrogen, or a combination thereof. In specific embodiments, the LHRH analog is leuprolide, goserelin, triptorelin, histrelin, or a combination thereof. In particular embodiments, the antiandrogen is flutamide, bicalutamide, nilutamide, or a combination thereof. In certain embodiments, treatment comprises abiraterone, MDV3100, Ipilimumab, bisphosphonate, leuprolide, or a combination thereof.

In certain embodiments of methods herein, the method further comprises the step of measuring the level of SRC-2 directly. In some cases, the level of SRC-2 is compared to the level of SRC-2 in normal cells. In certain embodiments, the level of SRC-2 mRNA is measured. The level of SRC-2 mRNA may be measured by RT-PCR, microarray, or RNA sequencing. In some cases, the level of SRC-2 protein is measured, such as by western, mass spectrometry, immunohistochemistry, or reverse-phase protein lysate microarray.

In one embodiments, there is a method of determining the risk of developing metastatic cancer in an individual, of determining that an individual has metastatic cancer, of determining a prognosis for an individual with cancer, and/or identifying a therapy for an individual with cancer, comprising the step of assaying a sample from the individual for the level of SRC-2 by measuring the level as follows: administering $^{13}C$-labeled glutamine to the individual; obtaining a sample from the individual, wherein the sample is suspected of comprising or known to comprise cancer cells; and measuring the level of citrate m+5, citrate m+1, or the ratio of citrate m+5/citrate m+4 from the cells, wherein when the level of citrate m+5, citrate m+1, or the ratio is elevated compared to a reference, the individual is at risk for developing metastatic cancer, has metastatic cancer, has a determined prognosis, or a therapy is identified for the individual. In specific embodiments, the cancer is of the prostate, breast, lung, liver, ovarian, endometrial, or colon. In some embodiments, the individual is treated for metastatic cancer or the individual is subject to treatment to prevent or delay the onset of metastatic cancer. In certain aspects, the prognosis is a poor prognosis. In specific embodiments, the identified therapy for the individual comprises inhibition of a SRC2-regulated pathway. In specific embodiments, the treatment comprises one or more SRC-2 inhibitors. Certain aspects of the method further comprise the step of determining that the individual has the cancer.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

FIG. 1—SRC-2 promotes lipogenesis in prostate tumor cells primarily from glutamine sources. (A) Western blot analysis showing the expression of SRC-2 and actin in C4-2 cells stably expressing non-targeting shRNA (shNT), and two different clones of SRC-2 shRNA (sh18 and sh19). Actin was used to normalize the protein loading. (B) Oil Red-O staining of C4-2 stable cells—shNT, sh18 and sh19 showing the neutral lipid content of the cells. Cells were counter-stained with nuclear-marker DAPI (4',6-diamidino-2-phenylindole) and merged images were shown on the right panel. (C) Quantitative analysis of the Oil Red-O stain. (D, E) Targeted mass spectrometry based-metabolomics analyses demonstrating the palmitoleic acid and oleic acid content of C4-2 cells treated with control-siRNA (siGFP) and two different SRC-2-siRNAs (siSRC-2#1 and siSRC-2#2). (F) Schematic representation of the carbon-flow into the TCA pathway from glucose and glutamine tracers. Blue arm of the pathway indicates the reductive carboxylation pathway. Enzymes indicated are: CS—citrate synthase, ACO—aconitase, IDH—isocitrate dehydrogenase. (G, H) C4-2 stable cells—shNT, sh18 and sh19 were cultured in presence of L-[U-$^{13}C_5$]glutamine for indicated time followed by metabolic flux analysis. Graphical representation shows the percentage incorporation of L-[U-$^{13}C_5$]glutamine-derived $^{13}C$ in palmitoleic and oleic acid at different time points. (I, J) C4-2 stable cells were cultured either in presence of L-[U-$^{13}C_5$]glutamine or D[U-$^{13}C_6$]glucose for indicated time followed by metabolic flux analysis. Comparative analysis of the total percentage of $^{13}C$ incorporation in oleic acid and palmitoleic acid obtained from glucose and glutamine sources. Data are graphed as the mean±s.e.m. *$P<0.05$, **$P<0.001$ by Student's t test. Scale bar 10 µm.

Figure 2:
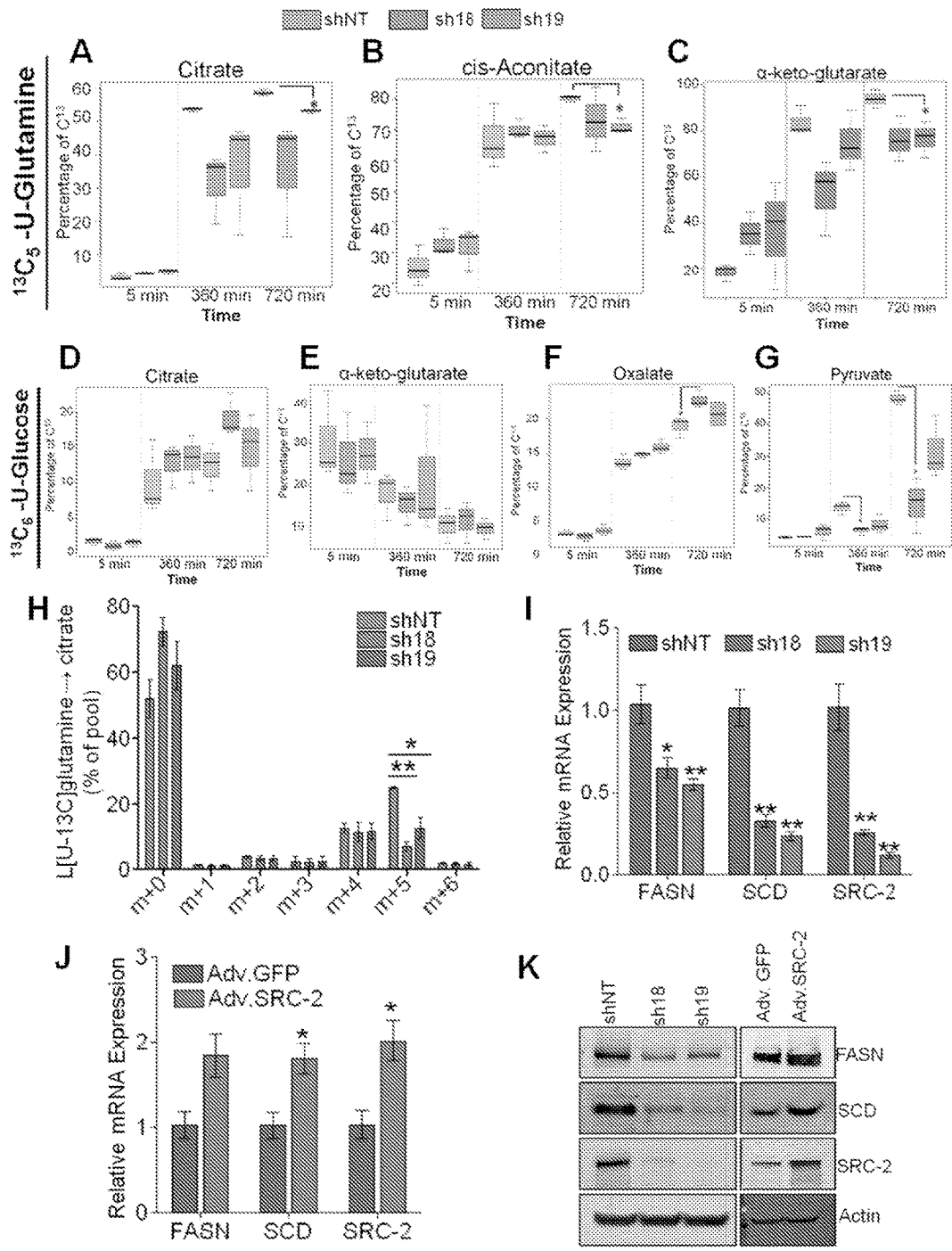

FIG. 2—SRC-2 generates citrate-flux by reductive glutamine metabolism. (A-C) Metabolites were extracted at indicated time-points from C4-2 stable cells—shNT, sh18 and sh19 cultured in presence of 2 mM-L-[U-$^{13}C_5$]glutamine and 11 mM of unlabelled glucose after addition of tracers. Metabolic flux analysis demonstrating the total percentage of glutamine-$^{13}C$ incorporated in citrate, cis-aconitate, and α-ketoglutarate. (D-G) Metabolites were extracted at indicated time-points from C4-2 stable cells—shNT, sh18 and sh19 cultured in presence of 11 mM D[U-$^{13}C_6$]glucose and 2 mM of unlabelled glutamine after addition of tracers. Metabolic flux analysis demonstrating the total percentage of glucose-$^{13}C$ incorporated in citrate, α-ketoglutarate, oxalate, and pyruvate. (H) Mass isotopomer analysis of citrate from C4-2 stable cells—shNT, sh18, and sh19 cultured in presence of 2 mM L-[U-$^{13}C_5$]glutamine and 11 mM unlabelled glucose for 6 hours after addition of tracers. (I) Quantitative real time PCR analysis of FASN, SCD, and SRC-2 gene expression in C4-2 stable cells—shNT, sh18, and sh19. (J) Quantitative real time PCR analysis of FASN, SCD, and SRC-2 gene expression in C4-2 cells expressing GFP (Adv. GFP) and SRC-2 (Adv. SRC-2) adenovirus. (K) Western blot analysis of FASN, SCD and SRC-2 in C4-2 stable cells—shNT, sh18, and sh19, and in C4-2 cells expressing Adv.GFP or Adv.SRC-2. Actin was used to normalize the protein loading. Data are graphed as the mean±s.e.m. *$P<0.05$, **$P<0.001$ by Student's t test.

Figure 3:
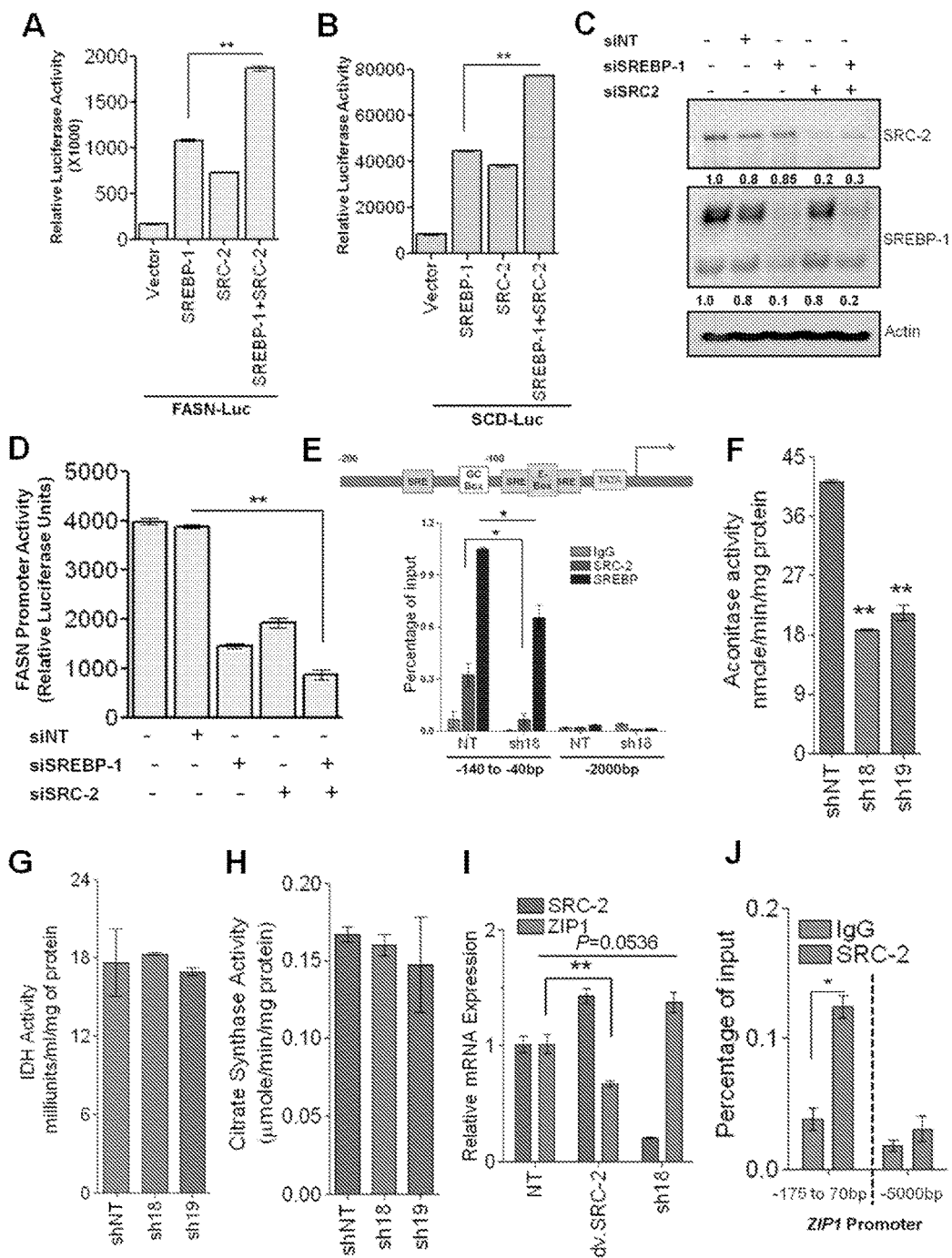

FIG. 3—SRC-2 promotes transcriptional alterations to sustain increased lipogenesis. (A) Luciferase reporter assay in HeLa cells transiently transfected with FASN-luciferase (FASNluc) construct (−220 to +25 bp) in presence of vector alone, SREBP-1, SRC-2, or combination of both SRC-2 and SREBP-1. (B) Luciferase reporter assay in HeLa cells transiently transfected with SCD-luciferase (SCDluc) construct (−1280 to +174 bp) in presence of vector alone, SREBP-1, SRC-2, or combination of both SRC-2 and SREBP-1. (C, D) Western blot analysis followed by luciferase reporter assay in PC-3 cells transfected with FASN-luc construct in presence of control-siRNA (siNT), SRC-2-siRNA (siSRC-2), SREBP-1-siRNA (siSREBP-1), or combination of both SRC-2 and SREBP-1. Semi-quantitative levels of each band were analyzed by densitometry using UVP Vision Works LS software and relative values (compared to untreated) normalized to actin are indicated numerically under each lane. (E) Chromatin immunoprecipitation assay (ChIP) of SRC-2 and SREBP-1 from C4-2 stable cells—shNT and sh18 showing the recruitment of these two proteins on FASN-promoter. The amplicons tested are either proximal promoter region (−140 to −40 bp) or an unconserved upstream region (−2000 bp) from the transcriptional start site. IgG antibody was used as control and data are presented as percentage of input chromatin. Cartoon shows the sterol regulatory element (SRE), GC box, E-box and TATA elements on FASN promoter. (F-H) Graphical representation of the enzyme activities of aconitase (ACO), isocitrate dehydrogenase (IDH), citrate synthase (CS) in C4-2 stable cells—shNT, sh18, and sh19. (I) Quantitative real time PCR analysis of SRC-2 and ZIP1 (SLC39A1) gene expression in C4-2 stable cells—shNT and sh18, and C4-2-shNT cells expressing adv.SRC-2. (J) ChIP of SRC-2 from C4-2 cells showing the recruitment of SRC-2 on ZIP1 proximal promoter (−175 to 70 bp) compared to −5000 bp upstream region from start site. Luciferase data were normalized to total protein. Data are graphed as the mean±s.e.m. *$P<0.05$, **$P<0.001$ by Student's t test.

Figure 4:
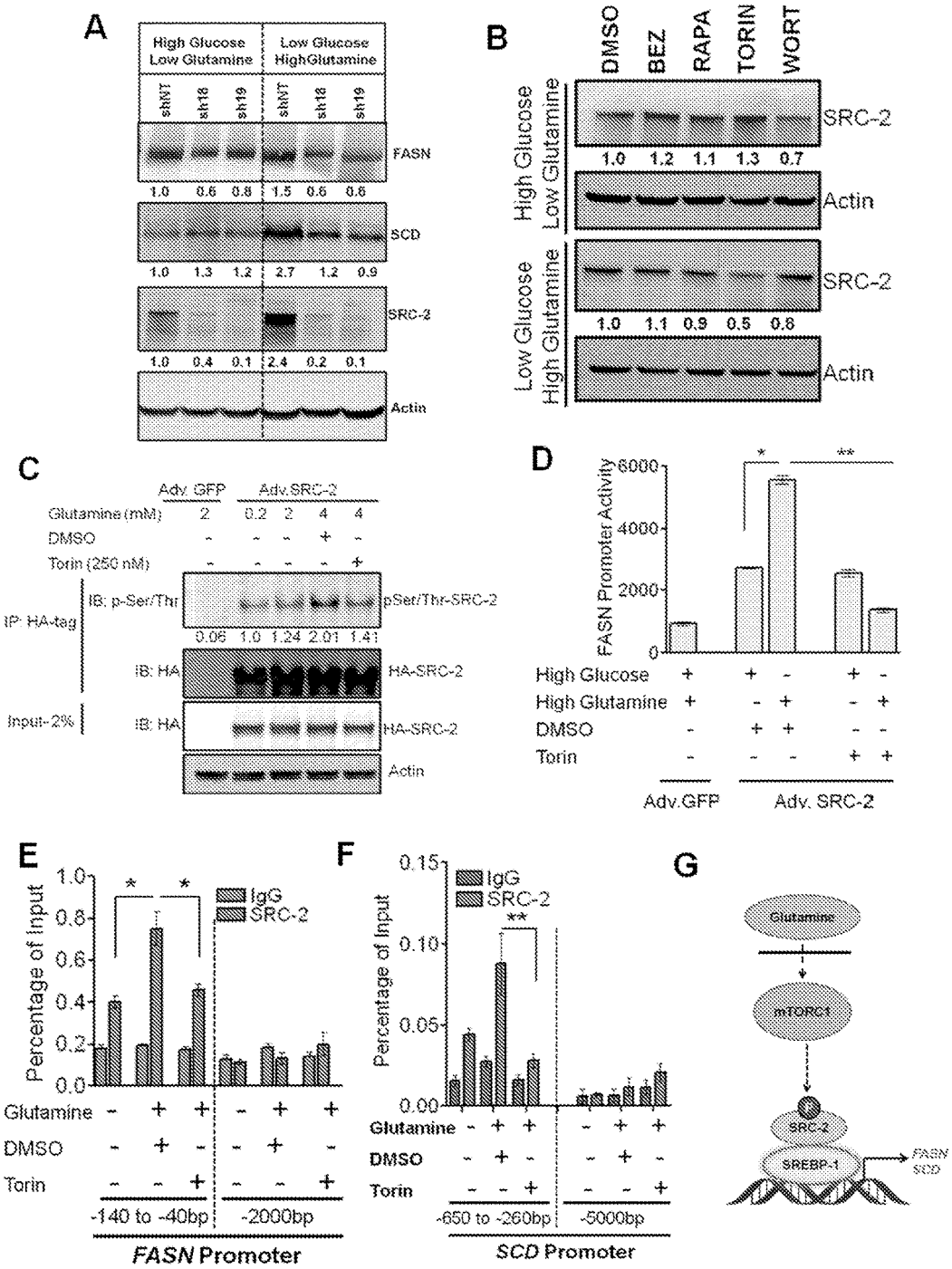

FIG. 4—Glutamine stimulation induces mTORC1-dependent SRC-2 transcriptional activity. (A) Western blot analysis of FASN, SCD, SRC-2 and actin in C4-2 stable cells—shNT, sh18 and sh19 grown in high glucose (11 mM)/low glutamine (0.2 mM) or low glucose (5 mM)/high glutamine (2 mM). Actin was used as a control to normalize the protein loading. Semiquantitative levels of each band were analyzed by densitometry using UVP Vision Works LS software and relative values (compared to shNT) normalized to actin are indicated numerically under each lane. (B) C4-2 cells were cultured in presence of high glucose (11 mM)/low glutamine (0.2 mM) or low glucose (5 mM)/high glutamine (2 mM) and then treated with kinase inhibitors: BEZ-235 (1 uM); Rapamycin (100 nM); Torin (250 nM); and Wortmannin (250 nM). Western blot analyses were performed to measure the stability of SRC-2 protein. Semi-quantitative levels of each band were analyzed by densitometry using UVP Vision Works LS software and relative values (compared to DMSO) normalized to actin are indicated numerically under each lane. (C) Immunoprecipitation of HA-SRC-2 followed by Western immunoblot to detect the phosphorylation status of SRC-2 using phospho-serine/threonine antibody. Input lysates were obtained from C4-2 cells expressing Adv.GFP or Adv. SRC-2, and subsequently stimulated with increasing concentration of glutamine—0.2 nM, 2 nM, and 4 nM followed by treatment with DMSO or mTORC1 inhibitor-Torin (250 nM). Actin was used to normalize the input loading. Semiquantitative levels of phospho-SRC-2 were analyzed by densitometry using UVP Vision Works LS software and relative values (compared to lane 2) normalized to actin are indicated numerically under each lane. (D) PC-3 cells expressing either Adv.GFP or Adv. SRC-2 were transfected with FASN-luc construct and stimulated with high glucose (11 mM)/low glutamine (0.2 mM) or high glutamine (2 mM)/low glucose (5 mM) followed by treatment with DMSO or Torin (250 nM). Lucifrease assay was then performed to measure the FASN promoter activity and data were normalized to total protein. (E, F) ChIP of SRC-2 from C4-2 cells showing the differential recruitment of SRC-2 on FASN and SCD-promoter upon glutamine stimulation (2 mM) in presence or absence of Torin (250 nM). The amplicons tested are indicated in the figure. IgG antibody was used as control and data are presented as percentage of input chromatin. (G) Cartoon depicting the proposed glutamine-mTORC1 signaling pathway with SRC-2 as the key downstream mediator regulating transcriptional functions coactivating SREBP-1. Data are graphed as the mean±s.e.m. *P<0.05, **P<0.001 by Student's t test.

Figure 5:
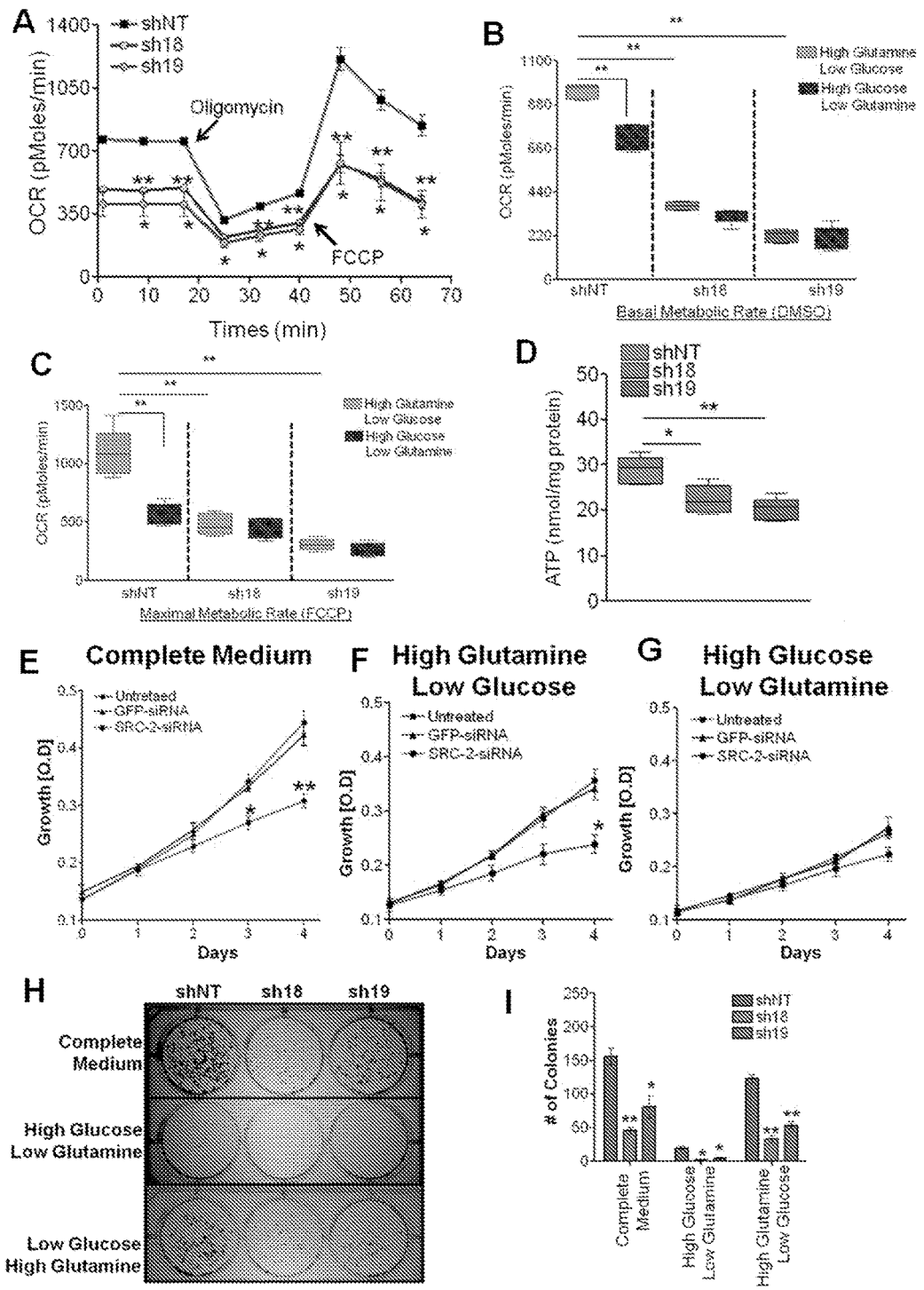

FIG. 5—SRC-2 defines the metabolic and energetic program of human prostate cancer cells. (A) Real-time measurement of basal and maximal oxygen consumption rate (OCR) in C4-2 stable cells—shNT, sh18 and sh19. (B, C) Basal and maximal OCR in C4-2 stable cells—shNT, sh18 and sh19 were measured in DMSO control (B) or FCCP-treated (C) cells cultured in presence of high glucose (11 mM)/low glutamine (0.2 mM) or low glucose (5 mM)/high glutamine (2 mM). (D) Intracellular ATP levels in C4-2 stable cells—shNT, sh18 and sh19 cultured in complete media. (E-G) Growth curve of C4-2 cells treated with control GFP-siRNA or SRC-2-siRNA, and cultured in complete medium (11 mM glucose and 2 mM glutamine); high glucose (11 mM)/low glutamine (0.2 mM); or low glucose (5 mM)/high glutamine (2 mM) for 4 days. (H) Clonogenic survival assay showing the number of C4-2 stable cell—shNT, sh18 and sh19 clones that survived during two weeks of nutritional stress. (I) Graphical representation of the total number of colonies as observed in cologenic survival assay shown in (H). Data are graphed as the mean±s.e.m. *P<0.05, **P<0.001 by Student's t test.

Figure 6:
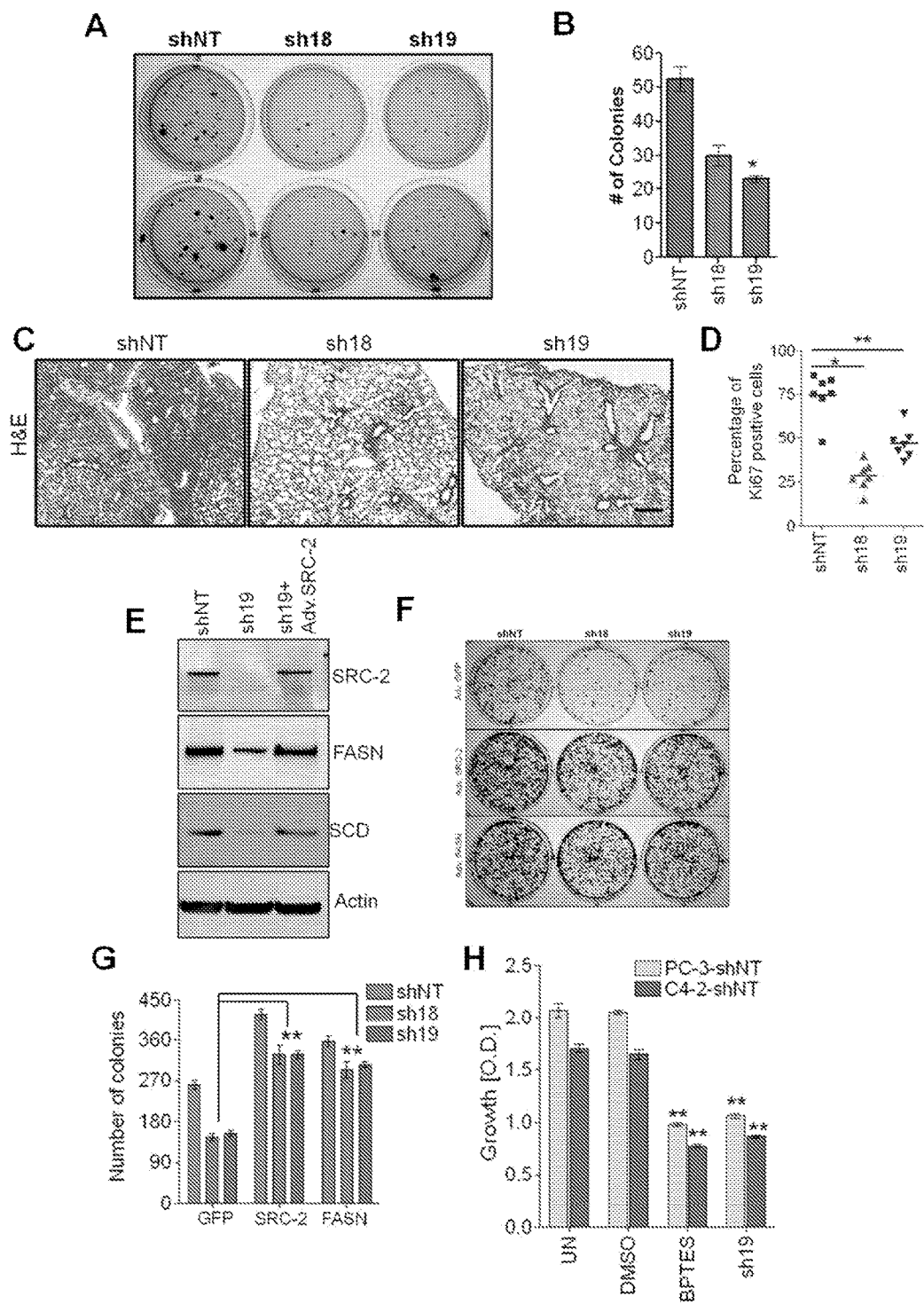

FIG. 6—SRC-2 is essential for prostate cancer cell survival. (A) Representative images depicting the growth of C4-2 stable cells—shNT, sh18 and sh19 in soft agar assay two weeks after plating. (B) Quantification of the total number of C4-2 stable cell colonies that survived after two weeks. (C) H&E stained sections of mouse lungs from experimental lung metastasis assay. Nude mice were injected with PC-3 cells stably expressing shNT, sh18 and sh19 via tail vein (n=7), and growth and survival of the cells in mouse lungs were analyzed after 5 weeks. (D) Quantification of Ki67 (antibody epitope reacts with human Ki67 protein) stained cells in the mouse lung sections from shNT, sh18 and sh19-injected animals. Refer Supplementary FIG. 14C. (E) Western blot analysis showing the expression levels of SRC-2, FASN, SCD and actin in C4-2 stable cells—shNT and sh19, and re-expression of SRC-2 in sh19 cells infected with Adv. SRC-2. Actin was used to normalize the protein loading. (F) Clonogenic survival assay in PC-3 stable cells—shNT, sh18 and sh19 expressing Adv.GFP, Adv.SRC-2 or Adv.FASN to rescue the defective survival phenotype in SRC-2-depleted cells. (G) Graphical representation of the number of colonies shown in (F). (H) Relative growth of C4-2 and PC-3 stable cells—shNT either untreated (UN), or treated with DMSO, BPTES (1 uM) for 4 days. sh19 cells were used to monitor effect of SRC-2 knockdown. Data are graphed as the mean±s.e.m. *P<0.05, **P<0.001 by Student's t test.

Figure 7:
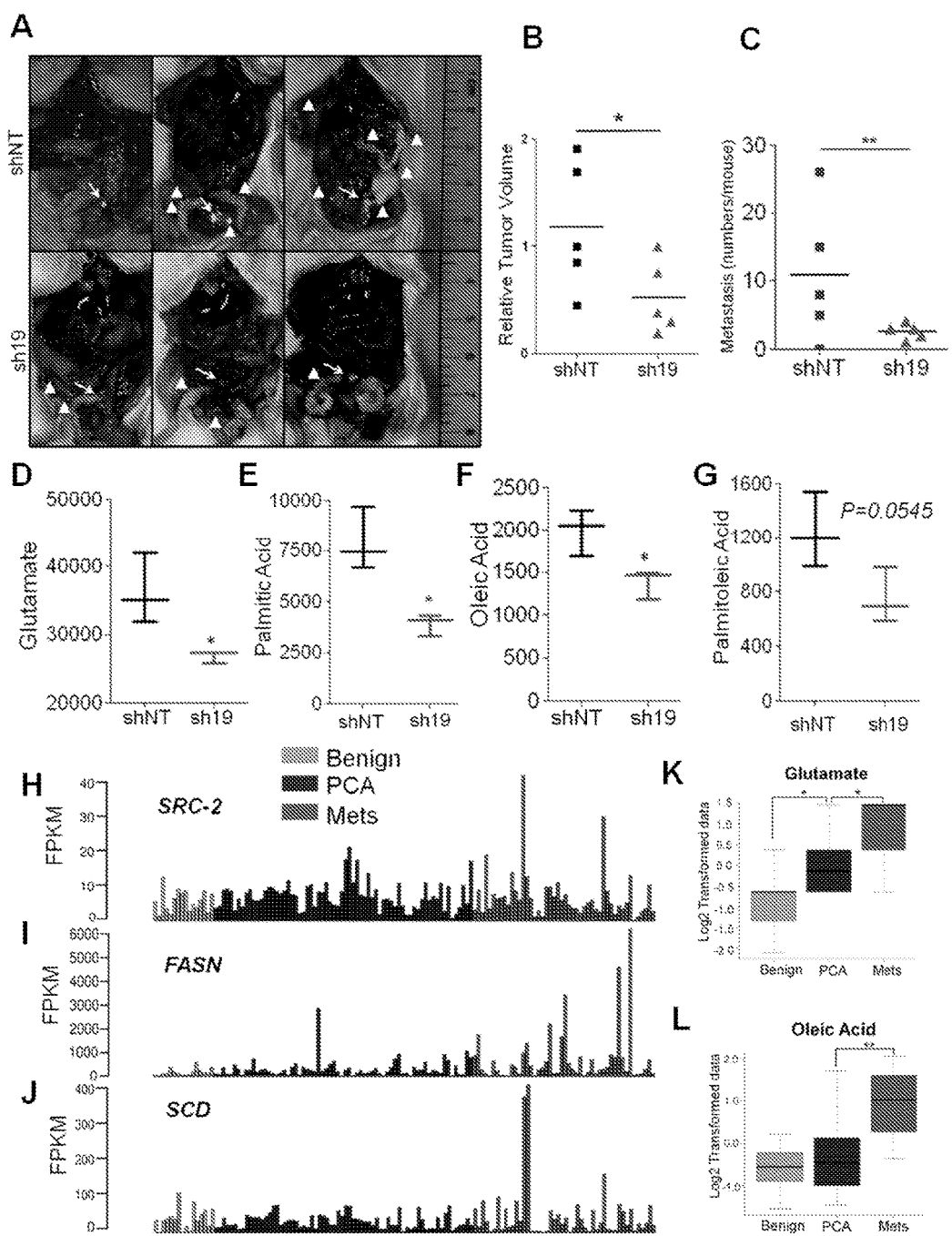

FIG. 7—SRC-2 promotes prostate cancer metastasis. (A) PC-3 stable cells expressing shNT and sh19 (n=5) were orthotopically implanted in the left ventral lobe of the SCID-mice prostate, and after 8 weeks post-surgery animals were sacrificed and imaged using UVP-Biospectrum imager. Merged images of GFP-fluorescence channel on white light are shown here. Arrows indicate primary tumor and arrow heads show the location of metastatic spread. (B) Each primary tumor was measured using slide calipers and relative tumor volumes were graphed. (C) Total number of metastatic spread visualized by the fluorescent imager were quantified and plotted to represent relative metastatic lesions in each mouse. (D-G) Targeted mass spectrometry based-metabolomic analysis of glutamate, palmitic acid, oleic acid and palmitoleic acid from isolated orthotopic prostate tumors of PC-3-shNT and sh19 as shown in (A). (H-J) FPKM values of SRC-2, FASN and SCD from RNA-seq data collected from a cohort of n=132 prostate samples collected from benign adjacent (n=16), organ confined prostate cancer (n=68) and metastatic prostate (n=48). (K, L) Log 2 Transformed data depicting the levels of glutamate and oleic acid in a cohort representing prostate tissues from benign adjacent prostate (n=16), clinically localized prostate cancer (n=12, PCA) and metastatic prostate cancer (n=14), as reported previously by (Sreekumar, et al., 2009). This cohort is a subset of the RNAseq cohort shown in H-J. Data are graphed as the mean±s.e.m. *P<0.05, **P<0.001 by Student's t test. For metabolomic analyses shown in K and L, the normalized data was taken from (Sreekumar, et al., 2009). There was performed a permutation based P-value (10000 permutation of sample labels) to define the significance of metabolites in different categories. The data was further plotted using boxplot in R language.

Figure 8:
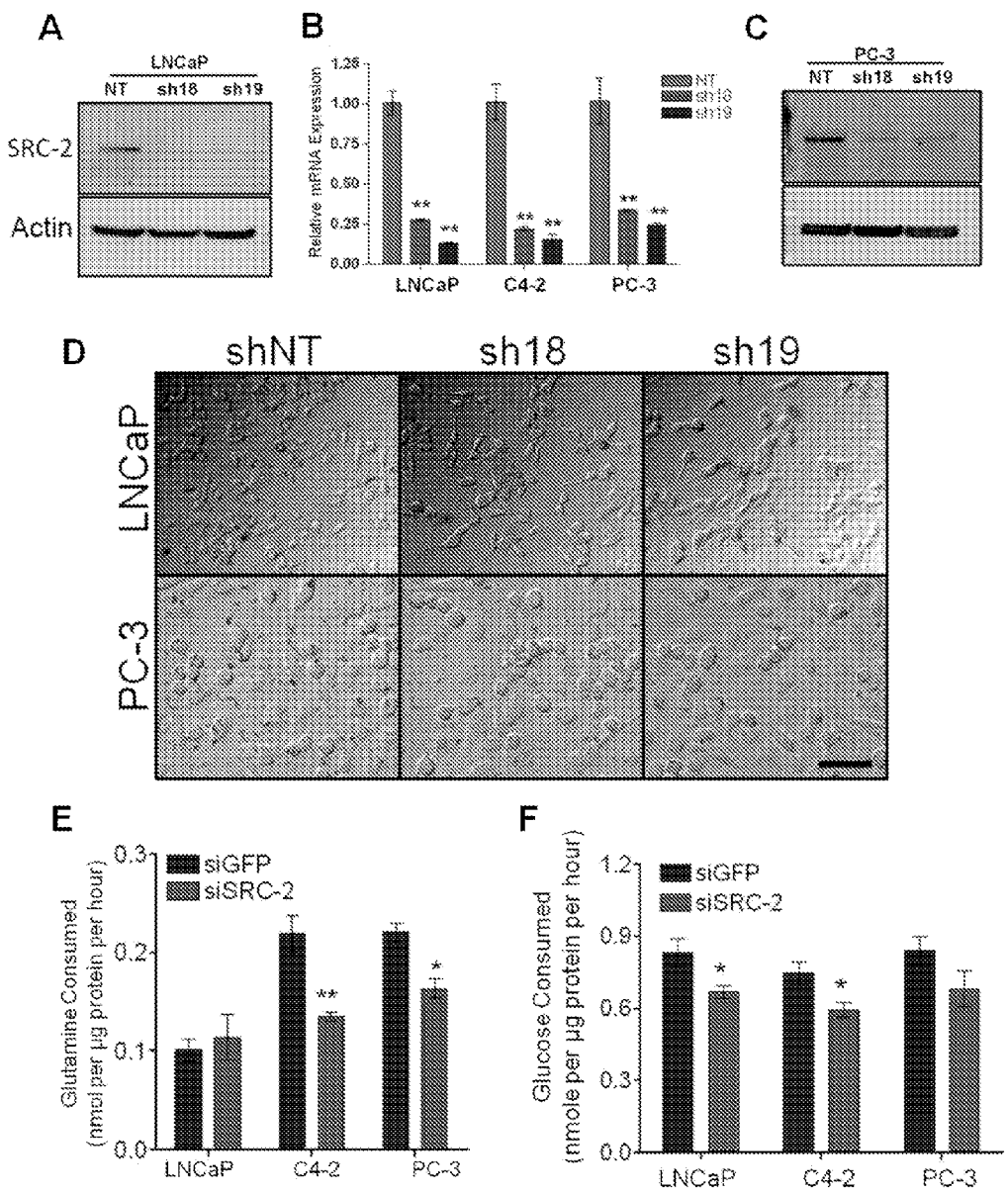

FIG. 8—SRC-2 ablated prostate cancer cells show reduced lipid droplet formation and decreased glutamine consumption. (A, C) Western blot analysis showing the expression of SRC-2 and actin in LNCaP and PC-3 cells stably expressing non-targeting shRNA (shNT), and two different clones of SRC-2 shRNA (sh18 and sh19). Actin was used to normalize the protein loading. (B) Quantitative real time PCR analysis of SRC-2 gene expression in LNCaP and PC-3 stable cells—shNT, sh18 and sh19. (D) Oil Red-O staining of LNCaP and PC-3 stable cells—shNT, sh18 and sh19. (E, F) Relative consumption of glucose and glutamine in LNCaP, C4-2 and PC-3 cells treated with control-siRNA (siGFP) or SRC-2-siRNA (siSRC-2). Data are graphed as the mean±s.e.m. *P<0.05, **P<0.001 by Student's t test. Scale bar 10 m.

Figure 9:
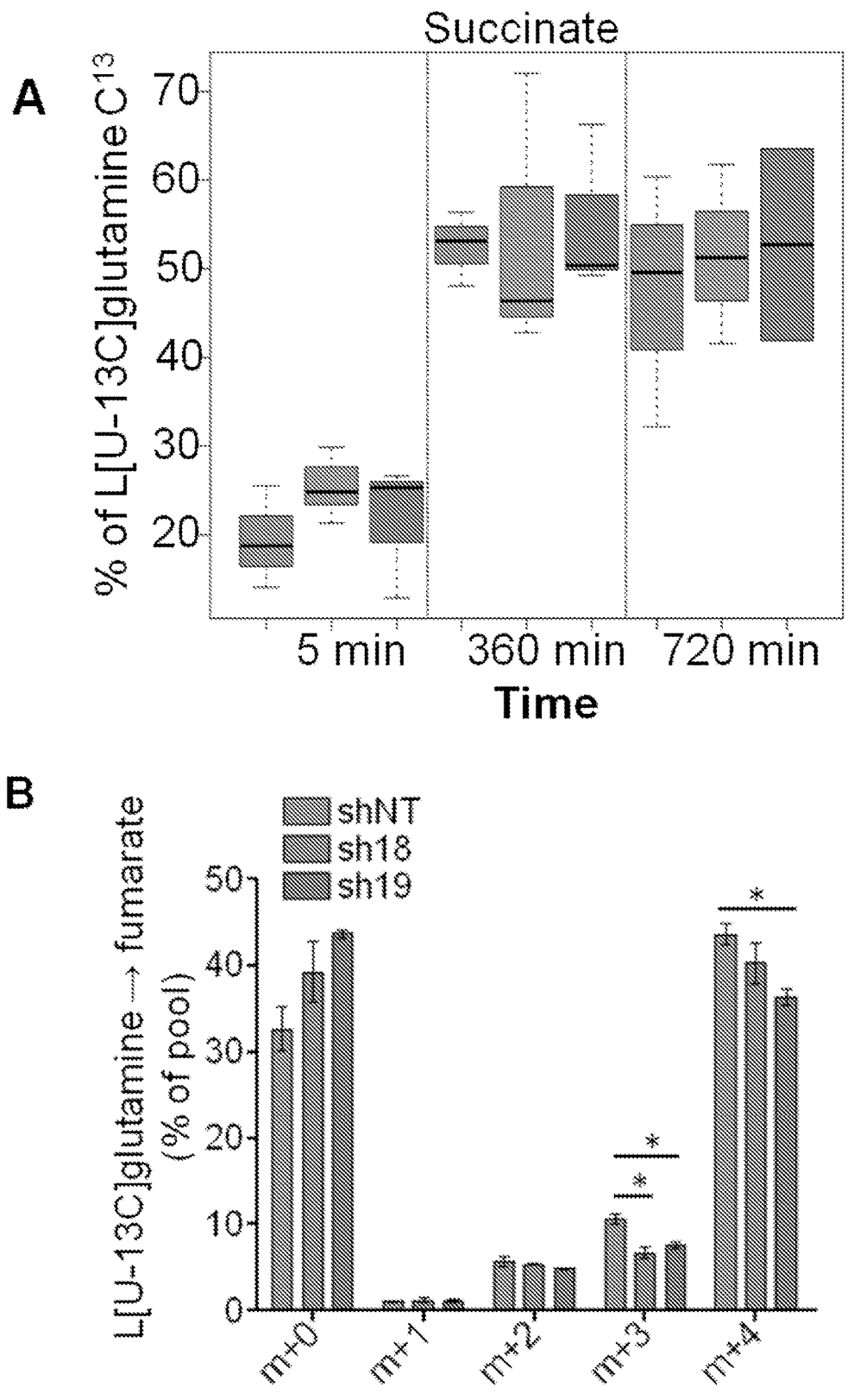

FIG. 9—Mass isotopomeric analysis of TCA metabolites in C4-2 stable cells. C4-2 stable cells—shNT, sh18 and sh19 were cultured in presence of 2 mM L-[U-$^{13}$C$_5$]glutamine and 11 mM unlabelled glucose, and metabolites were extracted after indicated time points. (A) Percentage incorporation of [U-$^{13}$C$_5$]glutamine $^{13}$C in succinate. (B) Mass isotopomer analysis of fumarate at 6 hours time point. Data are graphed as the mean±s.e.m. *P<0.05, **P<0.001 by Student's t test.

Figure 10:
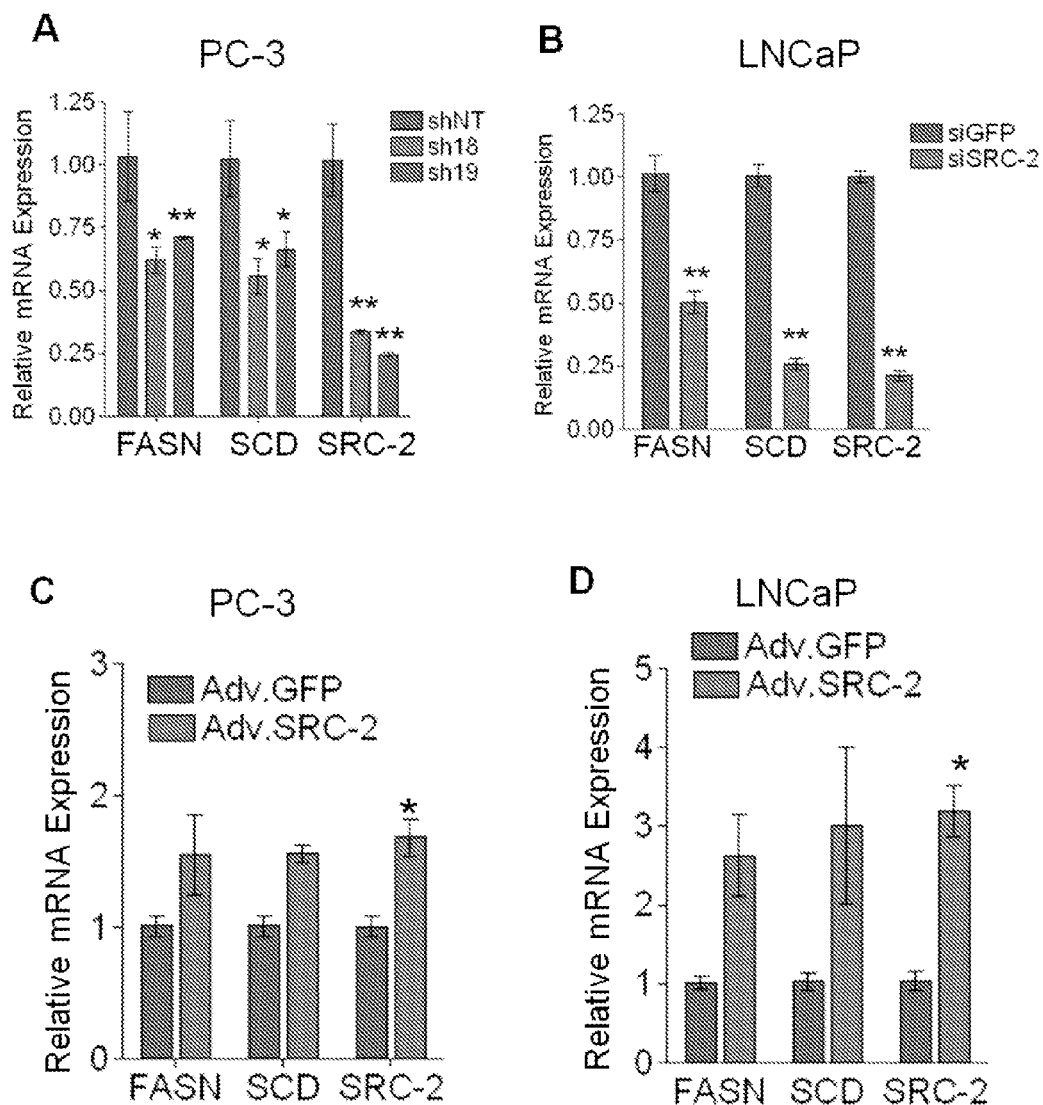

FIG. 10—SRC-2 regulates expression of FASN and SCD in prostate cancer cells. Quantitative real time PCR analysis of FASN, SCD, and SRC-2 gene expression relative to actin. (A) PC-3 stable cells expressing shNT, sh18, and sh19. (B) LNCaP cells treated with control siRNA (siGFP) or SRC-2-siRNA (siSRC-2), (C) PC-3 cells expressing control adenovirus (Adv.GFP) or SRC-2 adenovirus (Adv.SRC-2), (D) LNCaP cells expressing control adenovirus (Adv.GFP) or SRC-2 adenovirus (Adv.SRC-2). Data are graphed as the mean±s.e.m. *P<0.05, **P<0.001 by Student's t test.

Figure 11:
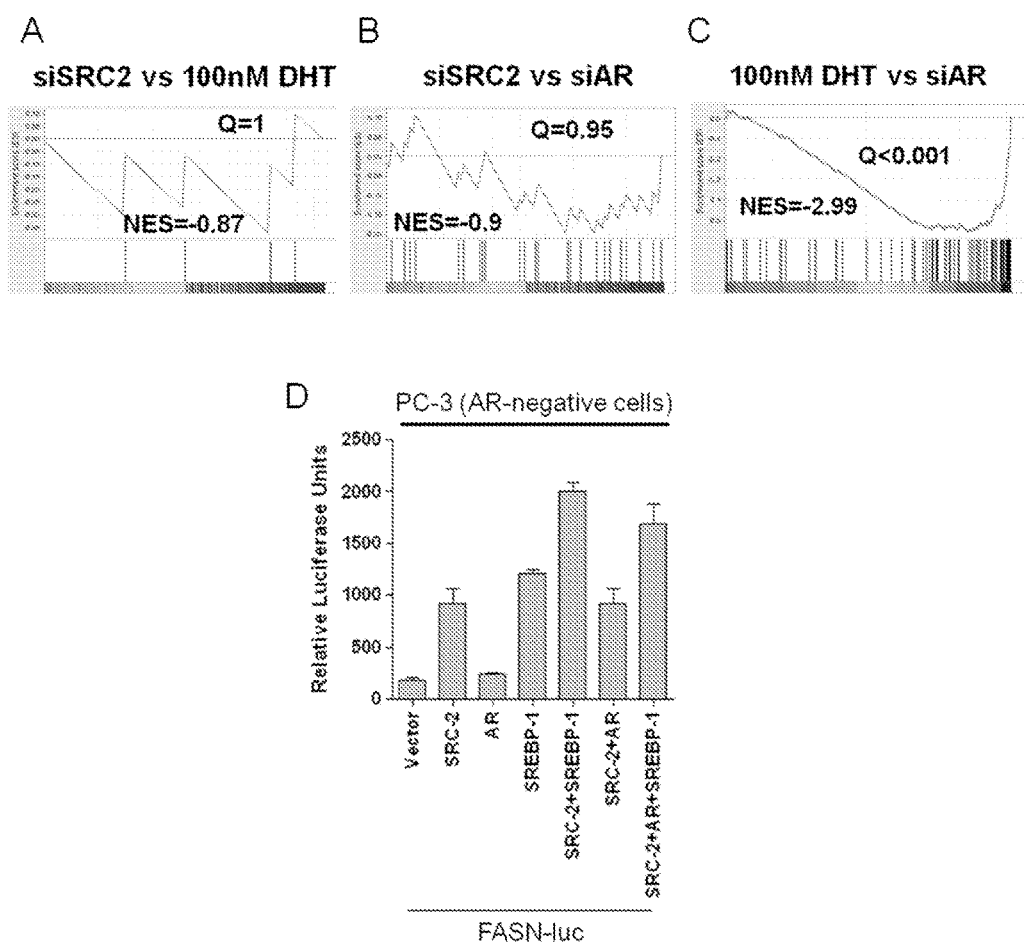

FIG. 11—SRC-2 transcriptionally regulates fatty acid biosynthetic genes independent of AR. Comparison of gene set enrichment analysis (GSEA) of siSRC-2 and siAR gene signatures with androgen (100 nM of dihydroxytestosterone) responsive signatures. (A) siSRC2 vs. 100 nM DHT, 24 hrs, NES=, q=1; (B) siSRC-2 vs. siAR, NES=−0.9, q=0.95; (C) siAR vs. 100 nM DHT, 24 hrs, NES=−2.99, Q<0.001. (D) Luciferase reporter assay in PC-3 cells transiently transfected with FASN-luciferase construct along with empty vector (pcDNA3.1), SRC-2, AR, SREBP-1a, or in combination. Luciferase values normalized to protein level.

Figure 12:
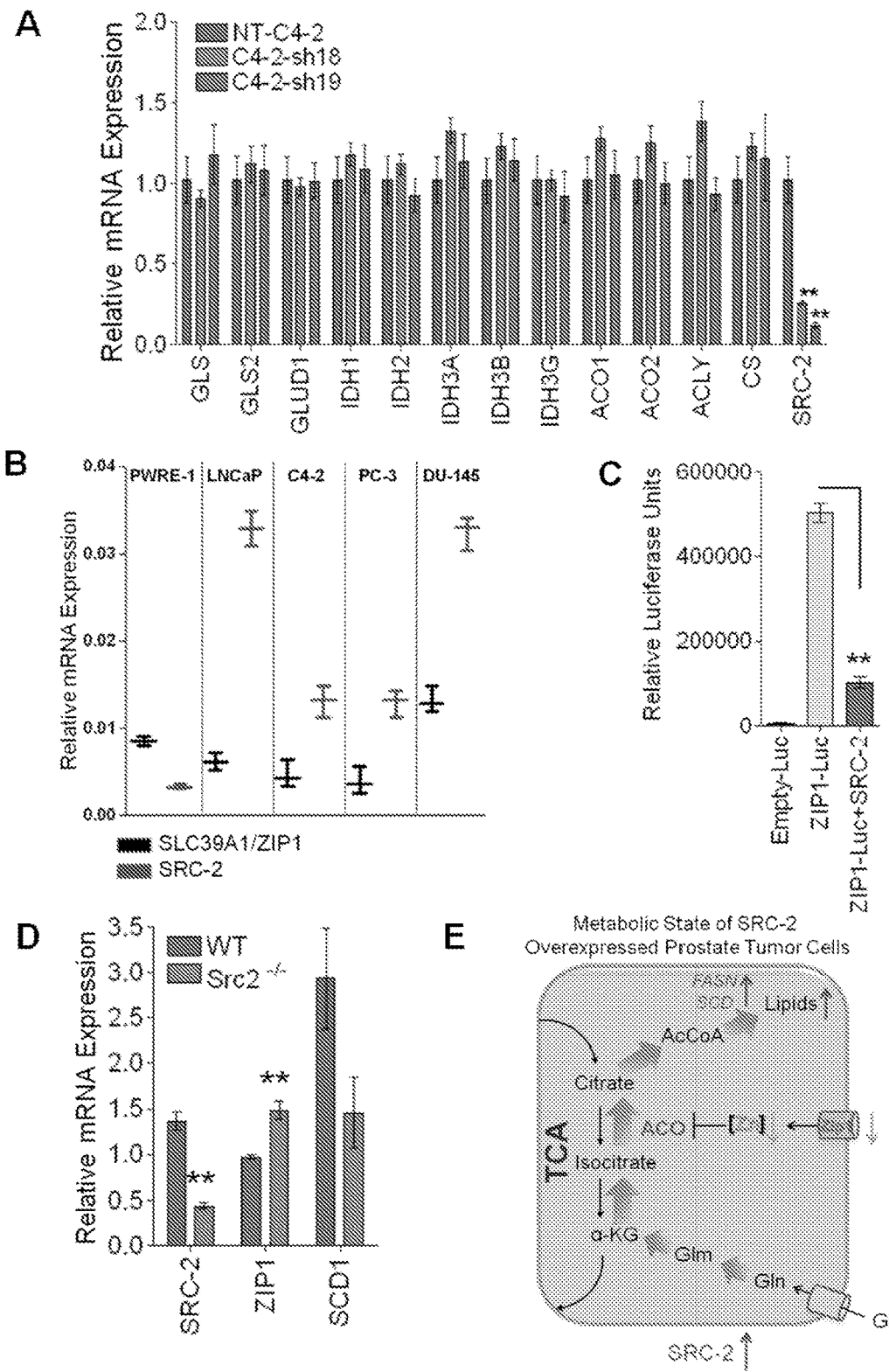

FIG. 12—SRC-2 represses ZIP1 (SLC39A1) expression to induce activation of aconitase enzyme. (A) Quantitative real time PCR analysis of GLS, GLS1, GLUD1, IDH1, IDH2, IDH3B, IDH3G, ACO1, ACO2, ACLY, CS and SRC-2 gene expression in C4-2 stable cells—shNT, sh18 and sh19. (B) Quantitative real time PCR analysis of SRC-2 and ZIP1 expression in transformed normal prostate epithelial cell line PWRE-1, and tumor lines LNCaP, C4-2, PC-3 and DU-145. Data are presented as relative fold expression normalized to actin. Data are graphed as the mean±s.e.m. *P<0.05, **P<0.001 by Student's t test. (C) Luciferase reporter assay in HeLa cells transiently transfected with empty pGL3 vector (Empty-Luc) and pGL3-ZIP1-luciferase (ZIP1-luc) construct (−246 to +82 bp) in presence of vector alone or SRC-2 construct. (D) Quantitative real time PCR analysis of Src-2, Zip1 (Slc39a1), and Scd1 from wildtype (WT) and SRC-2 knockout (SRC-2$^{-/-}$) mouse prostate (n=8). SCD1 was used as a control. (E) Cartoon depicting the proposed metabolic state of SRC-2 overexpressed prostate tumor cells. SRC-2 promotes glutamine (Gln) anaplerotic pathway by inducing reductive carboxylation of α-ketoglutarate (αKG) to generate citrate. This is facilitated by SRC-2 dependent repression of SLC39A1 (ZIP1), a Zn transporter thereby stimulating aconitase (ACO) enzymatic activity. Citrate is then converted into acetyl-CoA and eventually used for de novo lipogenesis by SRC-2 target enzymes FASN and SCD, thus promoting lipogenesis in prostate tumor cells.

Figure 13:
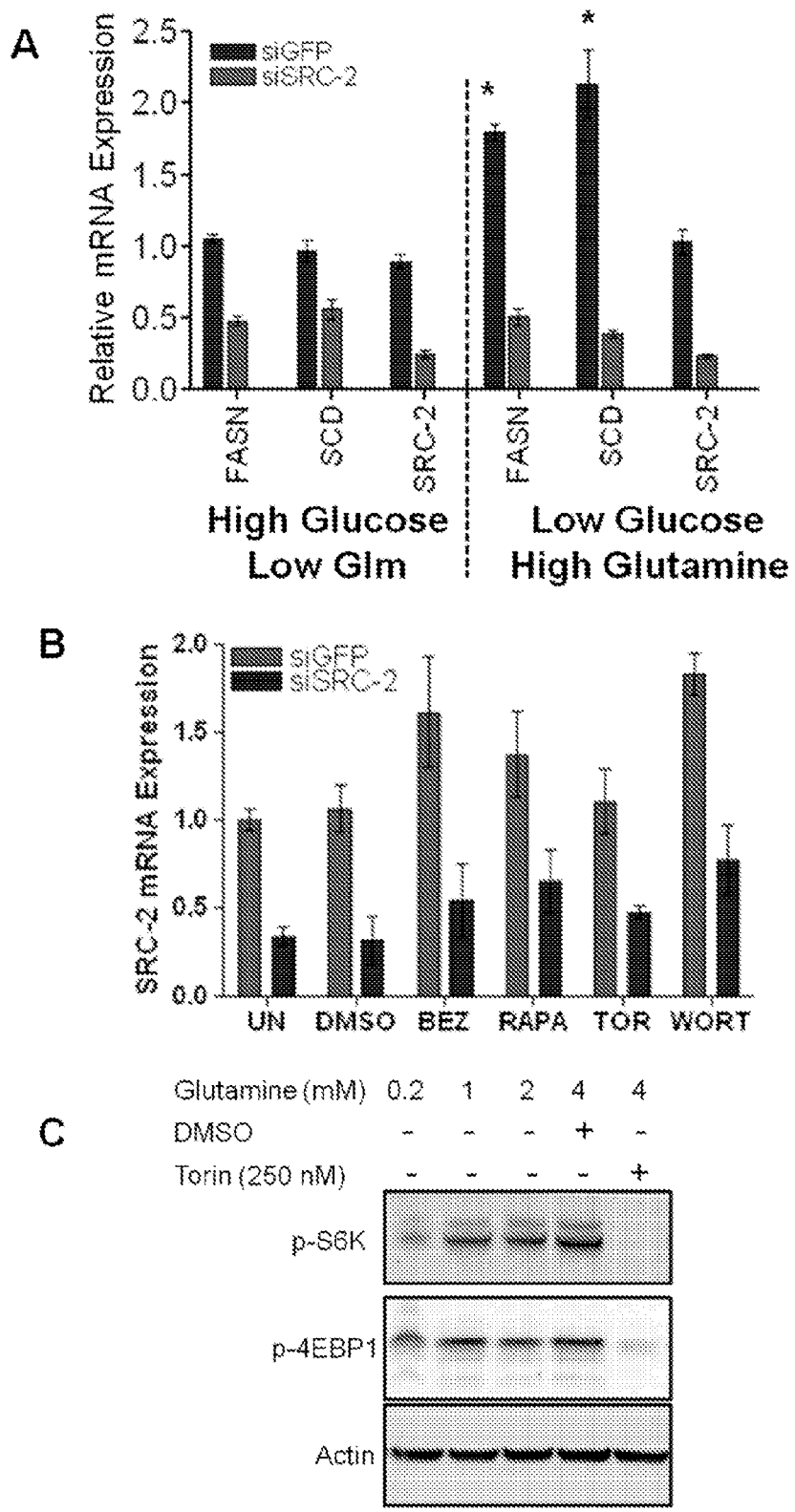

FIG. 13—Glutamine stimulation activates SRC-2 transcriptional functions in an mTORC1 dependent manner. (A) Quantitative real time PCR analysis of FASN, SCD and SRC-2 in C4-2 cells were treated with siGFP (control) or siSRC-2 and cultured in nutrient stressed conditions—high glucose (11 mM)/low glutamine (0.2 mM) or low glucose (5 mM)/high glutamine (2 mM). (B) Quantitative real time PCR analysis of SRC-2 in C4-2 cells expressing siGFP (control) or siSRC-2 and then treated with BEZ-235 (1 uM); Rapamycin (100 nM); Torin (250 nM); and Wortmannin (250 nM). (C) Western blot analysis showing the expression of phospho-S6K (p-S6K), phospho-4EBP1 (p-4EBP1) and actin in C4-2 cells stimulated with increasing concentration of glutamine followed by treatment with DMSO or mTORC1 inhibitor-Torin. Actin was used to normalize the protein loading.

Figure 14:
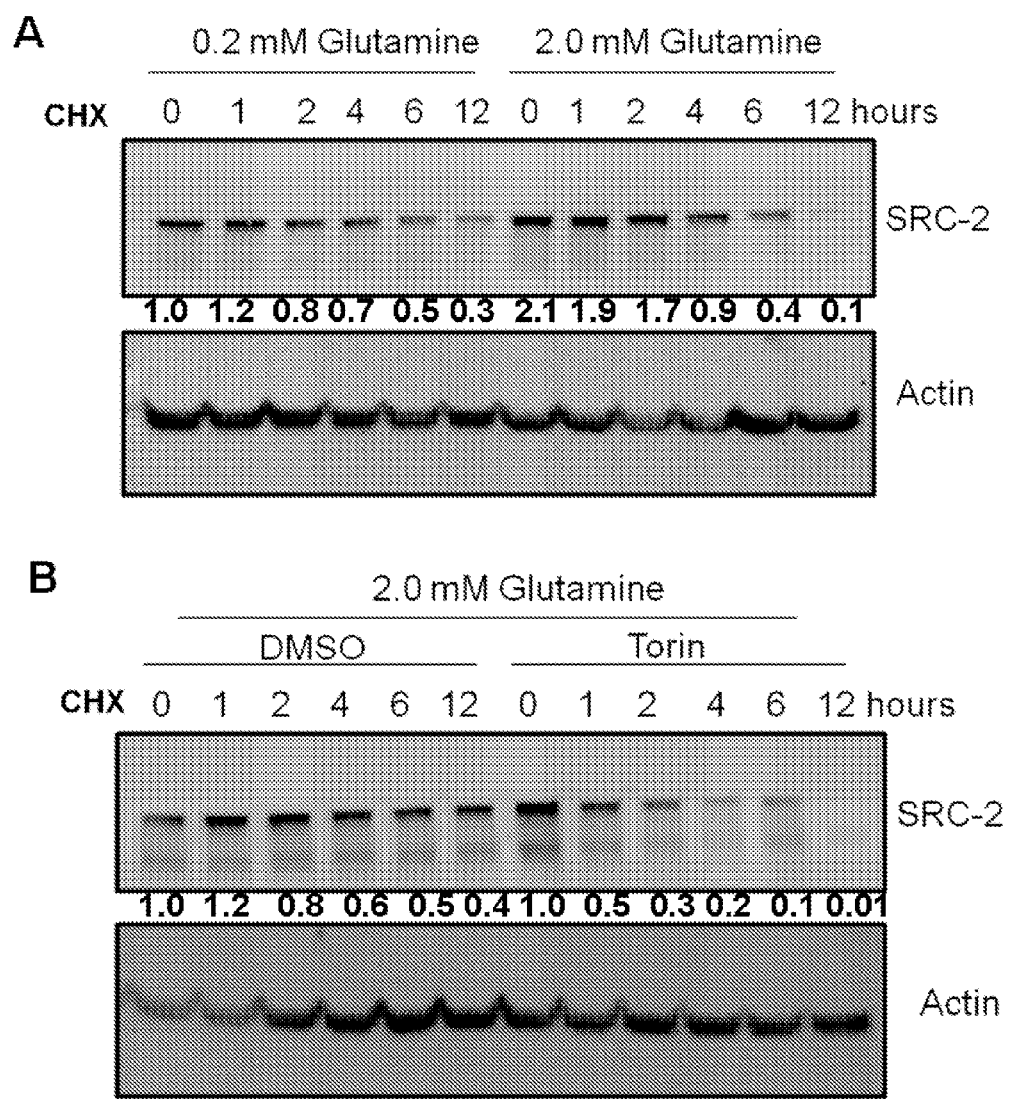

FIG. 14—Glutamine-dependent mTORC1 phosphorylation controls SRC-2 protein stability. (A) C4-2 cells were cultured in presence of low glutamine (0.2 mM) and high glutamine (2.0 mM) followed by treatment with cycloheximide (0.5 mM) for indicated time points. Western blot showing the total-level of SRC-2 and actin was used as a loading control. (B) C4-2 cells were cultured in presence of high glutamine (2.0 mM) followed by either treatment with DMSO and Torin. Cycloheximide (0.5 mM) was then added to the cells for indicated time points. Western blot showing the total-level of SRC-2 and actin was used as a loading control.

Figure 15:
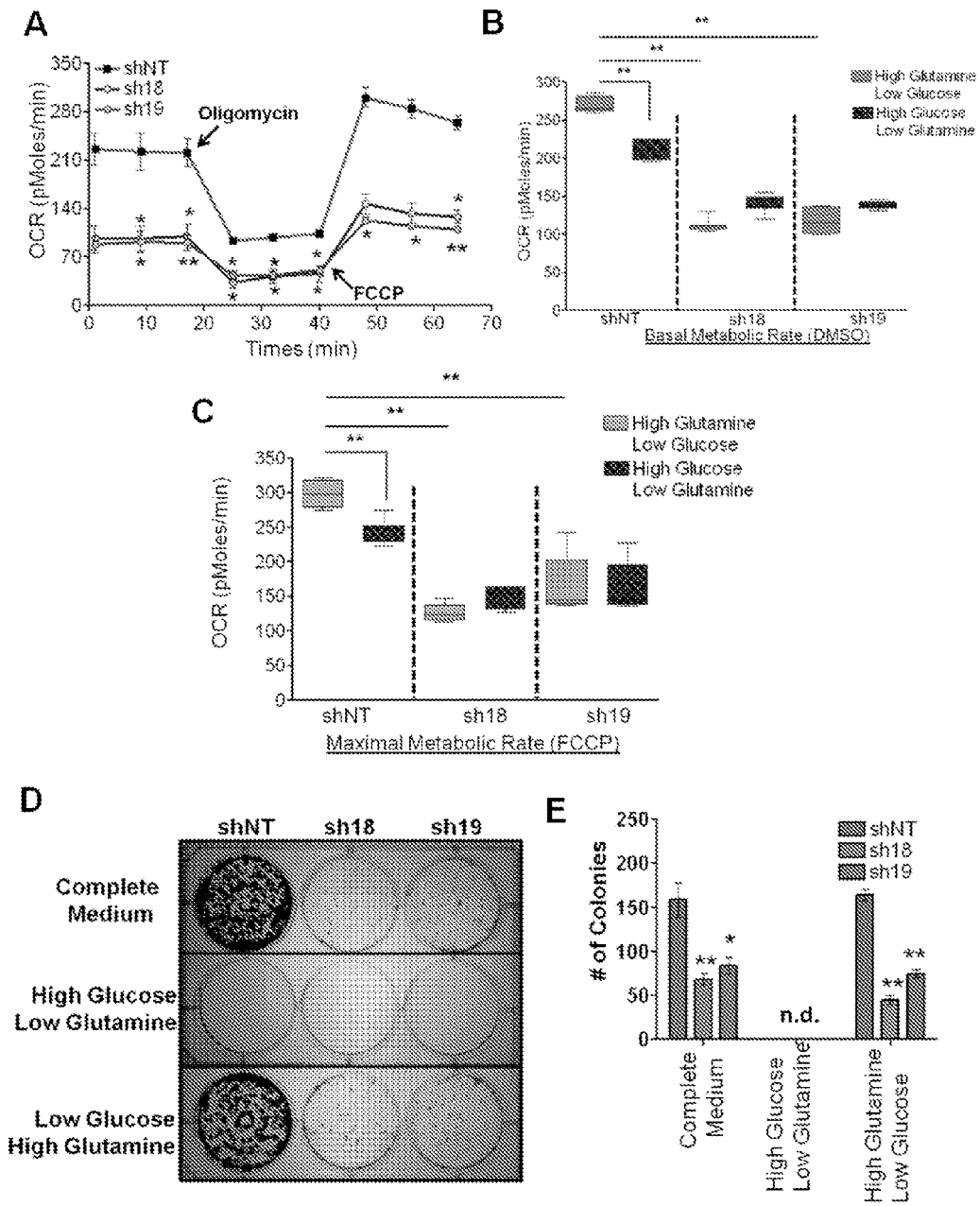

FIG. 15—Depletion of SRC-2 represents a metabolically deficient phenotype. (A) Real-time measurement of basal and maximal oxygen consumption rate (OCR) in PC-3 stable cells—shNT, sh18, and sh19. (B, C) Basal and maximal OCR in PC-3 stable cells—shNT, sh18, and sh19 were measured in DMSO control or FCCP-treated cells cultured in presence of high glucose (11 mM)/low glutamine (0.2 mM) or low glucose (5 mM)/high glutamine (2 mM). (D) Clonogenic survival assay showing the number of PC-3 cells stable cell—shNT, sh18, and sh19 clones that survived after 2 weeks of nutrient stress. (E) Graphical representation of the number of colonies shown in (D). Data are graphed as the mean±s.e.m. *P<0.05, **P<0.001 by Student's t test.

Figure 16:
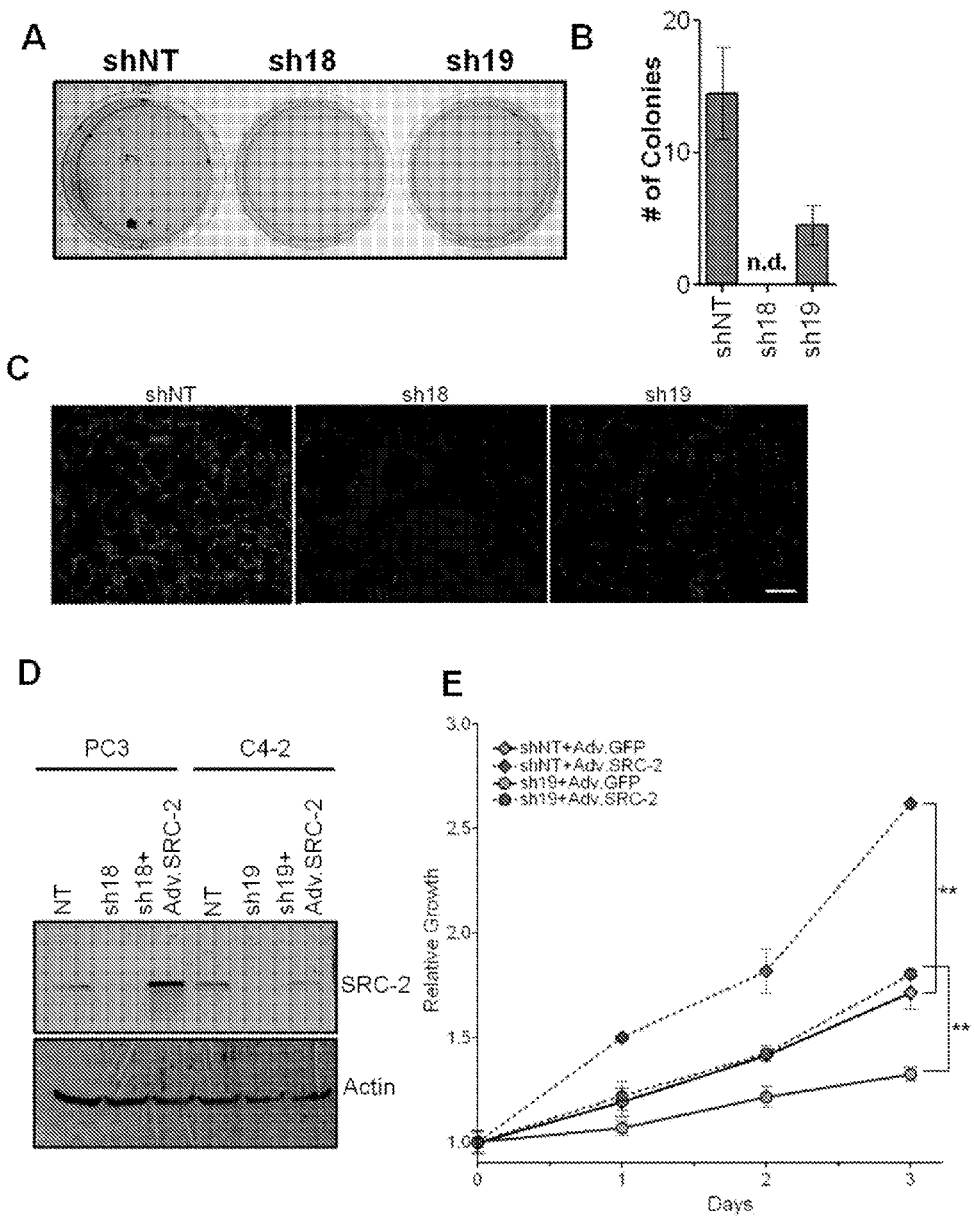

FIG. 16—Depletion of SRC-2 impairs prostate cancer cell survival. (A) Anchorage independent growth of PC-3 stable cells—shNT, sh18, and sh19 in soft agar assay two weeks after plating. (B) Graphical representation of the number of stained colonies in PC-3 stable cells—shNT, sh18, and sh19. N.D. stands for not determined. (C) Representative images of Ki67 stained mouse lungs sections from PC-3-shNT, sh18 and sh19-injected animals. (D) Western blot analysis showing the expression of SRC-2 and actin in PC-3 stable cells—shNT, sh18, and sh18 infected with Adv. SRC-2; and C4-2 stable cells—shNT, sh19 and sh19 infected with Adv. SRC-2. Actin was used to normalize the protein loading. (E) Growth curve of C4-2 stable cells—shNT and sh19 infected with either Adv. GFP or Adv. SRC-2. Data are graphed as the mean±s.e.m. *P<0.05, **P<0.001 by Student's t test. Scale bar 10 m.

Figure 17:
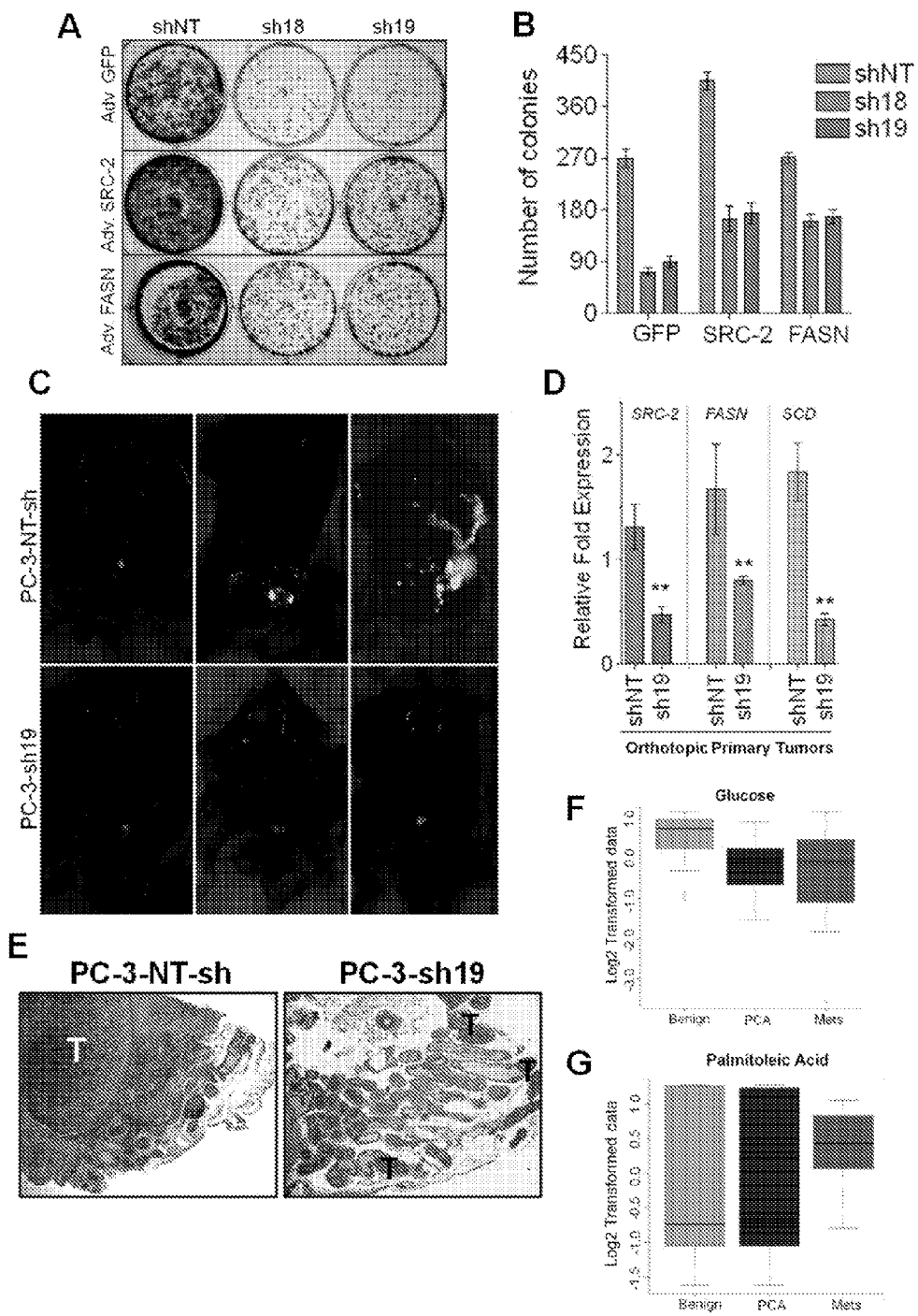

FIG. 17—Rescue by overexpression of SRC-2 or FASN restores survival deficiency of SRC-2-depleted prostate cancer cells. (A) Clonogenic survival assay in PC-3 stable cells expressing Adv.GFP, Adv.SRC-2 or Adv.FASN to rescue the defective survival phenotype in SRC-2-depleted cells. (B) Graphical representation of the number of colonies shown in (A). (C) GFP-fluorescence images (excitation: 480 nm, and emission: 510 nm) showing the primary tumor and metastatic spread in SCID mouse injected with PC-3 stable cells—shNT and sh19 orthotopically in mouse prostate (merged images shown in FIG. 7A). (D) Quantitative real time PCR analysis of FASN, SCD and SRC-2 in PC-3 orthotopic primary prostate tumors expressing non-targeting shRNA (sh-NT) or SRC-2-shRNA-19 (sh19). (E) H&E stained sections of PC-3 orthotopic primary prostate tumors expressing non-targeting shRNA (sh-NT) or SRC-2-shRNA-19 (sh19). T—shows the tumor area. (F, G) Log 2 Transformed data depicting the levels of glucose and palmitoleic acid in cohort of prostate tissues from benign adjacent prostate (n=16), clinically localized prostate cancer (n=12, PCA) and metastatic prostate cancer (n=14), as reported before by (Sreekumar, Poisson, et al., 2009). Data are graphed as the mean±s.e.m. *P<0.05, **P<0.001 by Student's t test. For metabolomic analyses shown in K and L, the normalized data was taken from (Sreekumar, Poisson, et al, 2009). A permutation based P-value (10000 permutation of sample labels) was performed to define the significance of metabolites in different categories. The data was further plotted using boxplot in R language.

FIG. 18 Provides a table of the fold change of particular genes in the presence of siRNA-SRC-2.

Figure 19:
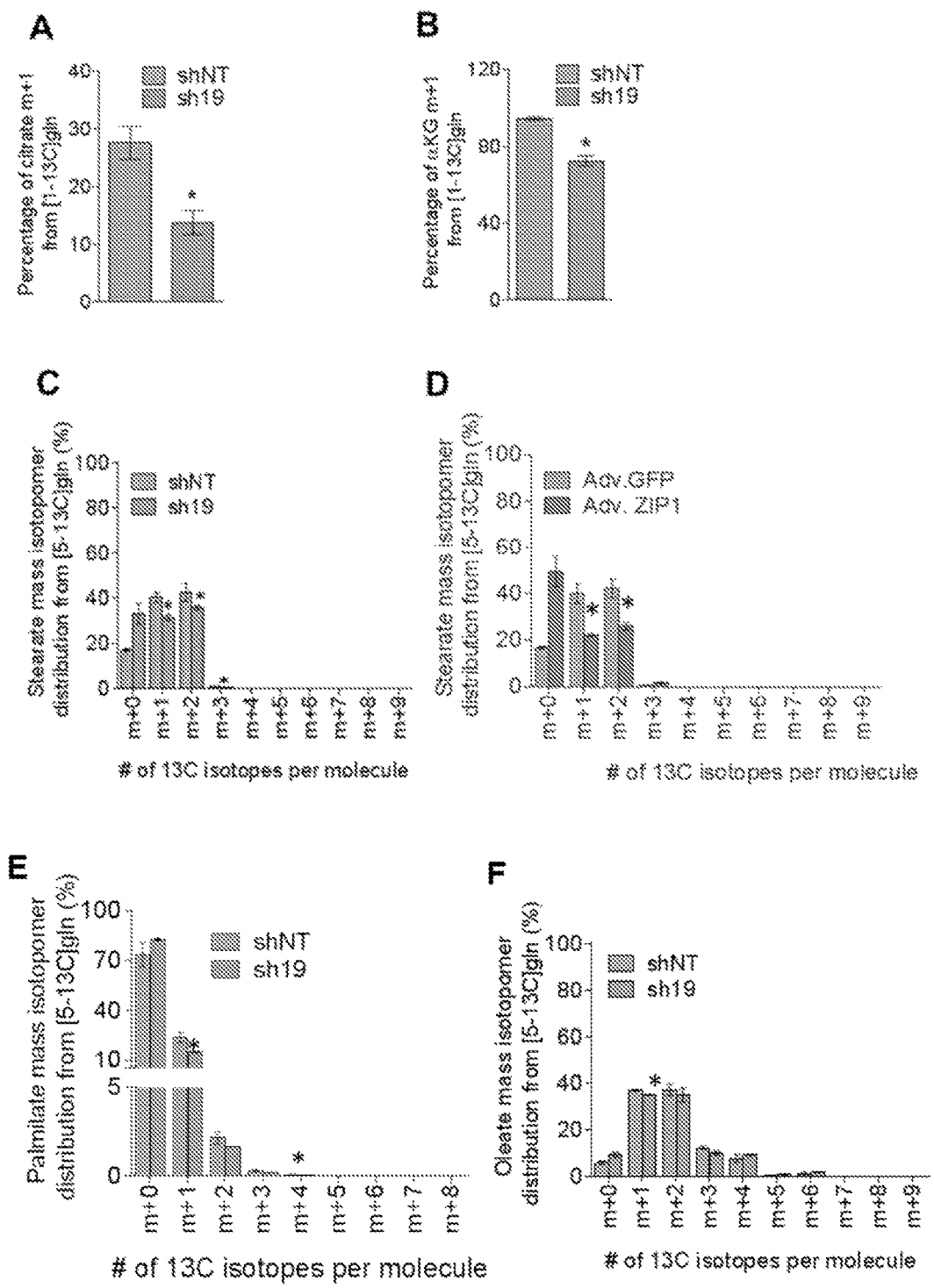

FIG. 19—$^{13}$C-Labeled glutamine, citrate, and α-ketoglutarate metabolism. (A,B) Citrate and α-ketoglutarate (α-KG) labelling from [1-$^{13}$C]glutamine in C4-2 stable cells—shNT and sh19 (n=3). (C) Mass isotopomer distribution of stearate labeling from [5-$^{13}$C]glutamine in C4-2 stable cells—shNT and sh19 (n=3). *P<0.05, by Student's t test with Holm-Sidak's multiple comparison test. (D) Mass isotopomer distribution of stearate labeling from [5-$^{13}$C] glutamine in C4-2 cells ectopically expressing human ZIP1 (Adv. ZIP1) or control virus (Adv. GFP) (n=3). Student's t-test with Holm-Sidak's multiple comparison test. (E,F) Mass isotopomer distribution of palmitate and oleate, respectively, labeling from [5-$^{13}$C]glutamine in C4-2 stable cells—shNT and sh19 (n=3). *P<0.05, by Student's t test with Holm-Sidak's multiple comparison test.

DETAILED DESCRIPTION

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," "a further embodiment," "a certain aspect," a particular aspect," "a specific aspect," or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The terms "citrate m+5" and "m+5 citrate" as used herein refer to a citrate generated from a $^{13}$C-labeled glutamine, wherein the citrate has five of its six carbons labeled with $^{13}$C.

The terms "citrate m+4" and "m+4 citrate" as used herein refer to a citrate generated from a $^{13}$C-labeled glutamine, wherein the citrate has four of its six carbons labeled with $^{13}$C.

The terms "citrate m+11" and "m+1 citrate" as used herein refer to a citrate generated from a $^{13}$C-labeled glutamine, wherein the citrate has one of its six carbons labeled with $^{13}$C.

I. General Embodiments

Cancer cells utilize various nutrients to support their unrestricted growth and survival. Glutamine is a major nutrient utilized by tumor cells to generate energy and biosynthesis of macromolecules required to support continuous growth and replication. One of the most important biomolecules synthesized from glutamine are lipids. Biochemically, five-carbon (5C) amino acid-glutamine is metabolized into 5C-α-ketoglutarate (α-kg), which then enters Tricarboxylic acid (TCA) cycle. In TCA-cycle, biochemical reactions include conversion of 5C-α-kg to 4C-succinate and then to 4C-fumarate, 4C-malate and 4C-oxaloacetate. 4C-oxaloacetate combines with 2C-acetate to generate 6C-citrate, which is the pre-cursor molecule for fatty acid biosynthesis. Citrate can either be used for fatty acid synthesis or may recycle back to generate 6C-isocitrate followed by 5C-α-kg. In addition to the above mentioned conventional TCA, some microbial cells and tumor cells can generate citrate from glutamine in a retrograde-TCA which is also known as 'reductive TCA'. In this process, 5C-glutamine derived 5C-α-kg is reversibly converted into 6C-citrate via 6C-isocitrate, using one molecule of carbon dioxide (1C). This pathway is a part of aggressive metastatic tumors, and the identification of its presence in cells is exploited for cancer analysis in methods of the disclosure.

Using $^{13}$C$_5$-labelled glutamine, evidence is provided herein that one can detect and measure 6C-citrate labeled with $^{13}$C$_5$, citrate m+5 if it follows reductive TCA or citrate m+4 if the canonical TCA path is followed. It is demonstrated herein that citrate m+5 level is higher in tumors with metastatic capabilities and is regulated by steroid receptor coactivator-2 (SRC-2). SRC-2 expression is significantly elevated in metastatic prostate tumors indicating that levels of citrate m+5 represent tumors with aggressive metastatic phenotypes. Detection of citrate m+5 levels or ratio of m+5/m+4 in patients with primary prostate tumors can thus diagnose/predict metastatic features early, and differentiate aggressive from indolent/localized tumors. This molecule would be produced in tumor cells rather than in normal cells, which do not have retrograde processing through the TCA cycle. The concept can be applied to the diagnosis of aggressiveness and metastatic potential for many different cancers and can be recovered by mass spectrometry (MS) (or other types of analysis from radioactive tracers, etc.) in urine or blood of patients, as an example. This information is of major importance for guiding therapeutic decisions. Using $^{13}$C$_1$-labelled glutamine, evidence is provided herein that one can detect and measure citrate labelled with a single $^{13}$C (citrate m+1) if it follows a reductive TCA pathway.

II. Analysis of Cancer by Methods of the Disclosure

Embodiments of the disclosure concern the analysis of one or more samples from an individual. The individual may be known to have cancer or may not be known to have cancer, but in specific embodiments the individual is known to have cancer and is in need of determining whether or not they have or will have metastatic cancer and, if so, determining an appropriate and effective therapy for the cancer.

The cancer may be of any kind, but in specific embodiments the cancer has an increased level of SRC-2 expression and/or activity or is suspected of having an increased level of SRC-2 expression and/or activity. In specific embodiments, the cancer is prostate, breast, lung, liver, ovarian, endometrial, or colon.

In embodiments of the disclosure, an individual known to have or suspected of having or being at risk of developing metastatic cancer is provided an effective amount of a tracer, such as a $^{13}$C-labeled tracer, and, in specific cases, the tracer is a labeled metabolite of a SRC-2-regulated pathway. In specific embodiments the labeled metabolite is $^{13}$C-labeled glutamine. The labeled tracer is uptaken by both normal and cancer cells, but the cancer cells are able to utilize a cancer-specific pathway wherein glutamine-derived alpha-ketoglutarate is reversibly converted into citrate via isocitrate using an additional carbon from carbon dioxide; such a pathway is identifiable by measuring a labeled metabolite therefrom that is unique in cancer cells. Once the tracer is provided to the individual and under sufficient conditions and for a sufficient duration of time (for example, one or more hours to one or more days), one or more appropriate samples are obtained from the individual to be utilized for analysis of one or more labeled metabolites.

Routes of administration of the $^{13}C$-labeled glutamine include any suitable kind, such as intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes).

In particular aspects, the sample from the individual is known to have cancer cells or is suspected of having cancer cells, and the cells in some cases the sample may or may not come from the primarily affected organ for the cancer. For example, in cases wherein the individual has prostate cancer, or even other types, urine or blood may be assayed for the presence of certain metabolites. The sample may be obtained by routine measures that would be dependent upon the type of sample required. In specific cases, the sample is urine, serum, blood, tissue biopsy, prostatic fluid, semen, nipple aspirate, feces, breath and other secretions or a mixture thereof. Some samples may be processed to remove undesired components that may interfere with the assay, and such processing is routine in the art. The samples may be stored and/or transported prior to analysis. Analysis of the samples may be performed by a party other than the party that interprets the results of the analysis. Obtaining the samples may be performed by parties other than that party or parties that performs analysis of the samples or interpretation of the outcome of the analysis.

In particular embodiments, technical analysis of the results of the method is performed using methods that recognize the employed label, such as at least by mass spectrometry, bioimaging using fluorescent-tagged dyes to the metabolite, or radioactive intensities using liquid scintillation counting, for example. The methods identify the presence of the labeled metabolite for which the assay is intended (such as citrate m+5, citrate m+4, citrate m+1, or a combination thereof). The presence of the metabolite, or the level of the metabolite, or a certain ratio of a metabolite with another, is indicative of metastatic cancer or the risk of developing metastatic cancer, in specific embodiments.

In specific embodiments, spectrometry-based detection of the tracer is employed, although in some cases, fluorescent-tagged metabolites uptaken by the tumor cells could be detected using PET imaging. In particular embodiments, a specific metabolite is measured, whereas in other cases the ratio of two metabolites is measured. In certain embodiments, the level of citrate m+5 or citrate m+1 is measured or the level of citrate m+5/citrate m+4 is measured. Such a level provides a result for the method, following which the result is utilized in determining a treatment for the cancer that otherwise may not have been known to be appropriate for the particular individual.

III. Treatment of Cancer

Following determination of the presence of, for example, citrate m+5, citrate m+1, or citrate m+5/citrate m+4 or particular levels thereof that are indicative of metastatic cancer or the risk thereof, a specific treatment for cancer is determined. That is, a certain level or presence of citrate m+5, citrate m+1, or citrate m+5/citrate m+4 indicates that the individual has metastatic cancer or is at risk for having metastatic cancer, and such knowledge dictates a specific type of therapy that otherwise may not have been given to the individual without such knowledge.

In specific embodiments, the therapy is useful for the treatment or prevention of metastatic cancer, and the skilled artisan recognizes that such a therapy for metastatic cancer is often not necessarily the same therapy as that for non-metastatic cancer from the same organ or tissue of origin.

In particular embodiments, the therapy targets a metabolite of a SRC-2 regulated pathway, including therapy that targets SRC-2 itself. In specific embodiments, one or more SRC-2 inhibitors are provided to the individual, such as one or more derivatives of bufalin are employed (Wang et al., 2014).

In certain embodiments, the therapy does not target a metabolite of a SRC-2 regulated pathway but nevertheless is suitable for metastatic cancer. Such therapy includes surgery, including radical surgery, chemotherapy, hormone therapy, immunotherapy, radiation, and so forth. Certain drugs useful for prostate cancer, for example, include LHRH analog, antiandrogen, or a combination thereof. Examples of LHRH analog include leuprolide, goserelin, triptorelin, histrelin, or a combination thereof. Examples of antiandrogen include flutamide, bicalutamide, nilutamide, or a combination thereof. Certain useful drugs for prostate cancer include abiraterone, MDV3100, Ipilimumab, bisphosphonate, leuprolide, or a combination thereof. In specific embodiments, the prostate cancer therapy comprises Abiraterone Acetate; Bicalutamide; Cabazitaxel; Casodex (Bicalutamide); Degarelix; Denosumab; Docetaxel; Enzalutamide; Jevtana (Cabazitaxel); Leuprolide Acetate; Lupron (Leuprolide Acetate); Lupron Depot (Leuprolide Acetate); Lupron Depot-3 Month (Leuprolide Acetate); Lupron Depot-4 Month (Leuprolide Acetate); Lupron Depot-Ped (Leuprolide Acetate); Prednisone; Prolia (Denosumab); Provenge (Sipuleucel-T); Radium 223 Dichloride; Sipuleucel-T; Taxotere (Docetaxel); Viadur (Leuprolide Acetate); Xgeva (Denosumab); Xofigo (Radium 223 Dichloride); Xtandi (Enzalutamide); Zytiga (Abiraterone Acetate), or a combination thereof.

In particular embodiments, a combination therapy comprises 1) one or more agents that target a metabolite of a SRC-2 regulated pathway and 2) one or more agents that target a metabolite of a SRC-2 regulated pathway is used.

In particular embodiments, one or more treatments are provided to the individual, including at separates times. Multiple doses of the therapy may be provided to the individual within days, weeks, or months of each other. In some cases, there are multiple doses of the same therapy, whereas in other cases there are multiple doses of two or more different therapies; in some cases, such combinations of two or more therapies may or may not be provided in alternating doses.

In particular aspects, one or more therapies are monitored using methods of the disclosure to ascertain the efficacy of the therapy. The therapy may or may not target a metabolite of a SRC-2 regulated pathway. In particular cases, the level of citrate m+5, citrate m+1, or citrate m+5/citrate m+4 is determined before and after one or more treatments, and following the one or more treatments a sample is analyzed for a change in the level of citrate m+5, citrate m+1, or citrate m+5/citrate m+4. In cases wherein a therapy is effective, the level of citrate m+5, citrate m+1, or citrate m+5/citrate m+4 will be reduced compared to the level of citrate m+5, citrate m+1, or citrate m+5/citrate m+4 prior to the therapy. In cases wherein a therapy is not effective because the level of citrate m+5, citrate m+1, or citrate m+5/citrate m+4 before and after therapy is not changed or has increased, an alternative one or more therapies may be employed.

IV. Pharmaceutical Preparations, Generally

In embodiments of the disclosure, there are methods of treating an individual that has been determined to have metastatic cancer, be at risk for metastatic cancer, or be susceptible to having metastatic cancer, for example. Those methods of treatment may include any kind, including pharmaceutical preparations to ameliorate one or more symptoms of metastatic cancer. In specific embodiments, the pharmaceutical preparation may include one or more agents that block a SRC-2 regulated metabolic pathway (including that inhibit SRC-2 activity and/or level) and/or one or more agents that treat metastatic cancer that do not block a SRC-2 regulated metabolic pathway (such as chemotherapy, hormone therapy, and/or immunotherapy, and so forth).

Pharmaceutical compositions of the present invention comprise an effective amount of one or more therapeutic agents dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one agent of the disclosure will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The agent may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include the agent and an appropriate solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the agent may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In preferred embodiments of the present invention, the agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations which are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, the agent may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneously, or intraperitoneally U.S. Pat. Nos. 6,7537, 514, 6,613,308, 5,466,468, 5,543,158; 5,641,515; and 5,399, 363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active agent may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Combination Therapy

In certain embodiments of the disclosure, treatment methods of the present disclosure are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with other therapy. In the context of the present disclosure, it is contemplated that the cell therapy could be used similarly in conjunction with chemotherapeutic, radiotherapeutic, and/or immunotherapeutic intervention.

Alternatively, the present inventive cell therapy may precede or follow the other agent treatment by intervals ranging from minutes to weeks. In embodiments where the other agent and present disclosure are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present disclosure is "A" and the secondary agent, such as radio- or chemotherapy, is "B":

| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination anti-cancer agents include, for example, acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estrarnustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin;

zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidenmin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin: neridronic acid; nilutamide; nisamycin; nitric oxide modulators; nitroxide antioxidant; nitrullyn; oblimersen (GENASENSE®); O.sup.6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer, or any analog or derivative variant of the foregoing and also combinations thereof.

In specific embodiments, chemotherapy for the individual is employed in conjunction with the disclosure, for example before, during and/or after administration of the disclosure.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics generally rely on the use of immune effector cells and molecules to target and destroy cancer cells, and immunotherapeutics other than the chimeric cytokine-expressing cells of the disclosure may be used, in certain embodiments. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

In certain other embodiments, the immunotherapy comprises use of an antibody against DLL4, Notch, or a Wnt pathway protein, for example.

D. Genes

In yet another embodiment, the secondary treatment is a gene therapy in which a therapeutic polynucleotide is administered before, after, or at the same time as the present disclosure clinical embodiments. A variety of expression products are encompassed within the disclosure, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present disclosure may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present disclosure to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

VI. Kits of the Invention

Any of the compositions described herein may be comprised in a kit. In a non-limiting example, one or more agents for use in treating cancer and/or one or more agents for determining the presence of cancer or characterizing one or more aspects of a cancer (such as its tendency to metastasize, the effectiveness of a therapy for the cancer, the prognosis for a patient with the cancer, and so forth) in a sample from an individual and/or the reagents to generate the agents may be comprised in a kit. The kit components are provided in suitable container means.

In specific embodiments, the kit comprises glutamine and a $^{13}$C radioisotope to generate $^{13}$C-labeled glutamine, or $^{13}$C-labeled glutamine that is already prepared. In certain embodiments, the kit alternatively or in addition comprises an agent that inhibits a SRC-2-regulated metabolic pathway, such as an agent that inhibits the activity and/or level of SRC-2. In certain embodiments, the kit alternatively or in addition comprises an agent that treats metastatic cancer, including at least metastatic prostate, breast, colon, ovarian, endometrial, or lung cancer. In some cases, the kit includes one or more reagents or apparatuses for obtaining a sample from an individual.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/or other diluent.

In particular embodiments of the disclosure, SRC-2 identifying agents and/or binding agents and/or inhibiting agents are provided in a kit, and in some cases one or more of the agents are essentially the sole component of the kit. The kit may comprise reagents and materials to make the desired composition. In specific embodiments, the reagents and materials include primers for amplifying desired sequences, nucleotides, suitable buffers or buffer reagents, salt, and so forth, and in some cases the reagents include vectors and/or DNA that encodes a gene product as described herein and/or regulatory elements therefor.

In particular embodiments, there are one or more apparatuses in the kit suitable for extracting one or more samples from an individual and/or for delivering therapeutic compositions to an individual. The apparatus may be a syringe, scalpel, and so forth.

In some cases of the disclosure, the kit, in addition to SRC-2-inhibiting agents, SRC-2-binding agents, and/or SRC-2 inhibiting agents also includes another cancer therapy, such as chemotherapy, hormone therapy, and/or another immunotherapy, for example. The kit(s) may be tailored to a particular cancer for an individual and comprise respective second cancer therapies for the individual.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

SRC-2 Regulates Lipogenesis by Reductive Glutamine Metabolism

Figure 1:
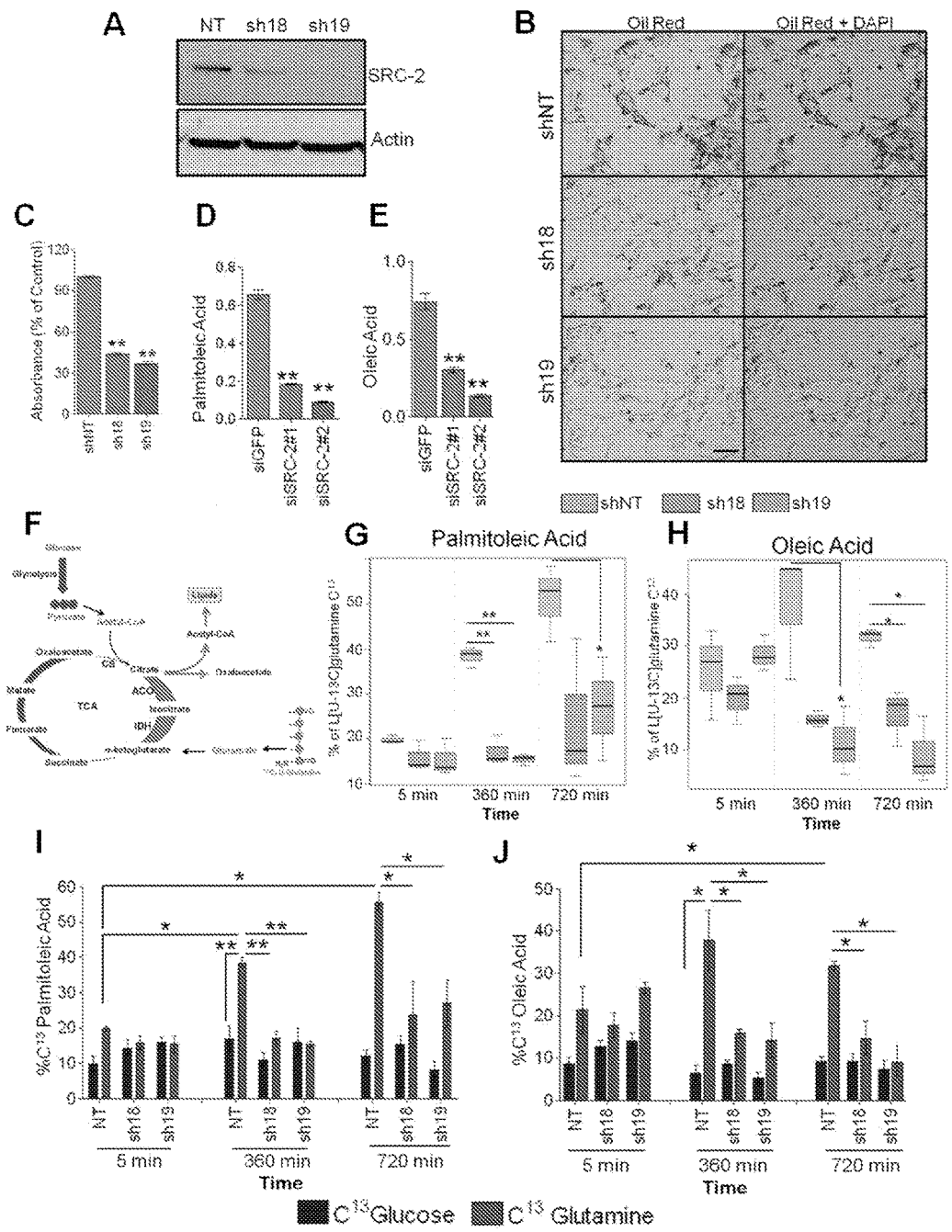

SRC-2 gene deletion studies in mice displayed severe metabolic defects particularly in fat accretion and energy homeostasis (Chopra, et al., 2008; Chopra, et al., 2011; Picard, et al., 2002; Duteil, et al., 2010). Because prostate cancer patients exhibit an increased dependency on fatty acids (Price, et al., 2002), SRC-2's role in prostate cancer lipogenesis was explored. To assess this, SRC-2 expression was stably impaired using two different clones of short hairpin RNA (sh18 and sh19) in three prostate cancer cell lines—LNCaP (FIGS. 8-A and 8-B), an androgen dependent cell line; C4-2 (FIGS. 1-A and 8-B), an androgen independent but responsive variant of LNCaP which represents the castration resistant subtype (Kosaka, et al., 2013; Liu, et al., 2004); and PC-3 (FIGS. 8-B and 8-C), an androgen receptor negative and highly metastatic line representing aggressive prostate tumors. Oil Red-O staining revealed a marked decrease in lipid accumulation due to SRC-2 knockdown in prostate cancer cells (FIGS. 1-B and 1-C; FIG. 8-D), and targeted metabolomic analysis identified significantly reduced fatty acid content (palmitoleic acid and oleic acid) in the total cellular metabolite pool (FIGS. 1-D and 1-E). Because glucose oxidation and glutamine metabolism are the two major carbon sources for fatty acid synthesis, the relative utilization of glucose and glutamine was compared in prostate cancer cells. C4-2 and PC-3 cells showed higher glutamine consumption compared to LNCaP, and SRC-2 ablation significantly reduced glutamine utilization in these cells, but not in LNCaP (FIG. 8-E). SRC-2 knockdown also showed alterations in glucose consumption, albeit minimally (FIG. 8F) when compared to glutamine utilization (FIG. 8-E).

To understand the biochemical steps affected by loss of SRC-2, C4-2 cells were cultured in the presence of uniformly labeled D[U-$^{13}$C$_6$]glucose or L[U-$^{13}$C$_5$]glutamine as tracers, and $^{13}$C enrichment was measured in intracellular metabolites (FIG. 1-F) by tandem mass spectrometry. Loss of SRC-2 dramatically decreased incorporation of glutamine-$^{13}$C in fatty acids, such as palmitoleic and oleic acid (FIGS. 1-G and 1-H). Surprisingly, in the control (shNT) cells there was a steep increase in glutamine-$^{13}$C enrichment in fatty acids with time but not glucose-$^{13}$C, indicating that prostate tumor cells were predominantly dependent on glutamine-derived carbon for biosynthesis of fatty acids, but not on carbon obtained from oxidation of glucose (FIGS. 1-I and 1-J). These findings indicate that glutamine is the major carbon donor for de novo lipogenesis in prostate cancer cells, and that SRC-2 plays a key role in regulating glutamine-dependent fatty acid biosynthesis.

Analysis of intermediary metabolites in the TCA-pathway revealed a substantial reduction in the total percentage of glutamine-derived $^{13}$C incorporation in citrate (FIG. 2-A), and a moderate decrease in cis-aconitate (FIG. 2-B) and α-ketoglutarate (FIG. 2-C) on SRC-2 depletion. However, SRC-2 knockdown had only minimal effects on glutamine-derived carbon incorporation in other TCA-metabolites such as succinate (FIG. 9-A). In contrast, D[U-$^{13}$C$_6$]glucose-derived-$^{13}$C did not show appreciable incorporation in TCA intermediates-citrate, α-ketoglutarate and oxalate (FIGS. 2-D to 2-F), but SRC-2 knockdown significantly decreased the $^{13}$C incorporation into pyruvate (FIG. 2-G), signifying a possible role of SRC-2 in the glycolytic pathway. [U-$^{13}$C$_5$] glutamine can contribute carbon to citrate either by oxidative metabolism generating citrate m+4 (where 'm' denotes nominal mass; m+4 indicates citrate containing four additional mass units derived from $^{13}$C) or by reductive carboxylation to generate citrate m+5 (Metallo et al., 2011; Mullen et al., 2011, Yoo et al., 2008). The latter reaction requires addition of an unlabelled carbon to glutamine derived α-ketoglutarate and a reversal in the enzymatic steps of isocitrate dehydrogenase (IDH) and aconitase associated with canonical oxidative TCA (FIG. 1-F). Analysis of citrate isotopomer revealed that the loss of SRC-2 expression had a minimal effect on citrate m+4, but significantly reduced the abundance of citrate m+5 levels (FIG. 2-H) indicating its role in reductive carboxylation pathway. Supporting this observation, there was significantly reduced fumarate m+3 in SRC-2 depleted C4-2 cells which are derivatives of citrate m+5, indicating role of SRC-2 in reductive-glutamine metabolism (FIG. 9-B). Taken together, these data reveal that SRC-2 reprograms metabolism of prostate cancer cells by diverting glutamine-flux through reductive-TCA, to support the increased demand of citrate for fatty acid biosynthesis.

In addition, [1-$^{13}$C]glutamine labeling provides more accurate measurement of reductive carboxylation of α-ketoglutarate to citrate, since this carbon is lost as carbon dioxide by alpha keto-dehydrogenase in the oxidative pathway, but retained if reductive carboxylation is active (Zhang et al.). Culturing C4-2 stable cells supplemented with [1-$^{13}$C]glutamine as tracers, enrichment of citrate m+1 was identified in control cells expressing non-targeting shRNA (shNT) whereas, ablation of SRC-2 showed a significant and robust decrease in the percentage of citrate m+1 (FIG. 19-A). In addition, SRC-2 knockdown also decreased the levels of α-ketoglutarate m+1 (FIG. 19-B), confirming that SRC-2 regulates the flow of carbon from glutamine to promote the reductive carboxylation of α-ketoglutarate in prostate cancer cells.

Next, the contribution of reductive carboxylation of glutamine-derived α-ketoglutarate towards lipogenesis was investigated. To trace this, C4-2 stable cells were labelled with [5-$^{13}$C]glutamine tracer since the [1-$^{13}$C]glutamine-derived isotopic label cannot be incorporated in acetyl-CoA through reductive carboxylation. [5-$^{13}$C]glutamine transfers only one $^{13}$C atom to acetyl-CoA and fatty acids through reductive carboxylation, but loses the $^{13}$C incorporation into the acetyl-CoA carbon skeleton via oxidative pathway. Consequently, [5-$^{13}$C]glutamine is specific to trace the reductive carboxylation to the lipid flux (Gameiro et al.). Labeling of C4-2 cells with [5-$^{13}$C]glutamine indicated that reductive carboxylation contributed to the flow of carbon from glutamine to fatty acids, and loss of SRC-2 significantly decreased the mass isotopomer distribution of the fatty acids such as stearate (FIG. 19-C), palmitate and oleate (FIG. 19-E). These findings indicate that glutamine contributes to de novo lipogenesis in prostate cancer cells via reductive carboxylation, and SRC-2 plays a key role in regulating the process.

Example 2

Transcriptional Reprogramming Supports Lipogenesis

To understand the mechanism of SRC-2 dependent lipogenesis in prostate cancer cells, targeted gene expression analysis was performed by quantitative-PCR of enzymes (derived from KEGG) involved in glucose and lipid metabolism, TCA cycle, and glutamine metabolism. SRC-2 depletion had a broad impact on the expression of metabolic genes, among which two genes fatty acid synthase (FASN) and stearoyl-CoA desaturase (SCD), were significantly reduced upon SRC-2 silencing (FIG. 18). FASN is a multifunctional enzyme that catalyzes the biosynthesis of long-chain fatty acids from acetyl-CoA and malonyl-CoA, whereas SCD is a desaturase enzyme that synthesizes unsaturated fatty acids by incorporating double bonds into the long-chain fatty acids (Menendez & Lupu, 2007). FASN and SCD have been implicated in the progression of various types of malignancies including prostate cancer (Menendez & Lupu, 2007), but the precise mechanism regulating their increased expression in cancer cells is less understood. Loss and gain-of-expression of SRC-2 altered FASN and SCD levels in prostate cancer cells (FIGS. 21, 2J, and 2K; FIGS. 10-A to 10-D), so the role of SRC-2 was further defined in the transcriptional regulation of these two genes. Although, SRC-2 is known to be a coactivator of AR, SRC-2-dependent transcriptional regulation of FASN and SCD was observed in both AR-positive (LNCaP and C4-2) and AR-negative cells (PC-3). To gain further insight into this, the enrichment of androgen-regulated genes in an LNCaP-siSRC2 gene signature was investigated using the GSEA method. The LNCaP-siSRC2 gene signature was compared with an androgen-induced (100 nM DHT) gene signature in LNCaP cells (Wang Q, Li W, et al, 2007) and also with a LNCaP-siAR gene signature. The siSRC2 regulated genes do not enrich for either the androgen-induced gene signature (NES=−0.87, Q=1) or for the siAR response signature (NES=−0.9, Q=0.95) (FIGS. 11A and 11B). In contrast, the androgen-induced gene signature is enriched significantly in the siAR gene signature (NES=−2.99, Q<0.001) (FIG. 11-C). These data support the notion that SRC-2 is not acting wholly via AR, and its association with other transcription factors is likely to be the explanation as to why SRC-2 is overexpressed to such a high level in aggressive prostate cancer.

Analysis of SRC-2 ChIP-Seq data revealed increased occupancy of SRC-2 on the FASN and SCD promoters (unpublished observations), which overlapped with sterol regulatory element binding protein-1 (SREBP-1) response elements (SRE) in the proximal promoter region (25). To directly test the effects of SRC-2 and SREBP-1 on FASN and SCD expression, luciferase reporter gene assays were performed using the FASN (−220 to +25 bp) (26) and SCD (−1280 to +174 bp) promoter constructs. Fitting with the effects observed on endogenous FASN and SCD expression, SRC-2 strongly activated the transcription at both promoters, and more so in combination with the SREBP-1 transcription factor (FIGS. 3-A and 3-B; FIG. 11-D). However, AR either alone or in combination with SRC-2 failed to activate the luciferase-driven FASN-promoter in AR-negative PC-3 cells, again indicating that SRC-2 is acting independent of AR (FIG. 11D). Similarly, silencing of SRC-2 either alone or in combination with SREBP-1 (FIG. 3-C) greatly impaired the FASN promoter activity in PC-3 cells (FIG. 3-D), suggesting that SRC-2 coactivates transcriptional activity of SREBP-1 on FASN and SCD promoters. Finally, chromatin immunoprecipitation (ChIP) assays confirmed strong occupancy of SRC-2 and SREBP-1 on the proximal promoter of FASN compared to an unconserved upstream region (FIG. 3-E). Interestingly, ablation of SRC-2 showed a modest decrease in the SREBP-1's occupancy on the FASN promoter (FIG. 3-E), which suggests that the recruitment of SRC-2 as a coactivator may facilitate stabilization of SREBP-1 on the chromatin. Together, these data confirm that SRC-2 transcriptionally regulates fatty acid biosynthetic genes primarily by coactivating SREBP-1, independent of AR.

Next, the mechanisms were investigated by which SRC-2 promotes reductive carboxylation of α-ketoglutarate to generate citrate-flux as indicated by metabolic flux analysis. Gene expression analysis of enzymes generating citrate from glutamine metabolism did not show any significant alterations upon SRC-2 depletion (FIG. 12-A). However, surprisingly there was a dramatic decrease in aconitase enzyme activity (FIG. 3-F) but not isocitrate dehydrogenase (IDH) or citrate synthase (CS) activities (FIGS. 3-G and 3-H) (Smolkova & Jezek, 2012), in SRC-2 depleted C4-2 cells compared to control-C4-2 cells. Aconitase catalyzes the stereo-specific isomerization of citrate to isocitrate via cis-aconitate, and this reversible reaction is allosterically regulated by the intracellular zinc concentration (Costello, et al., 1997). Interestingly, in normal prostate epithelial cells aconitase activity is impaired due to increased amounts of zinc, whereas in prostate tumor cells this blockage is reversed due to loss of a zinc transporter ZIP1 (SLC39A1) (Singh, et al., 2006). It was considered that SRC-2 may be the genetic cause for reduced expression of ZIP1 in prostate tumors, thus indirectly regulating aconitase activity. Indeed, ZIP1 expression was significantly higher in normal prostate cells compared to the majority of the tumor cell lines examined except DU145 (FIG. 12-B), and forced expression of SRC-2 reduced endogenous ZIP1 expression (FIG. 3-I) by directly binding to the proximal promoter region (FIG. 3-J) and repressing gene transcription (FIG. 12-C). Supporting this observation, there were higher levels of ZIP1 expression in SRC-2-knockout mouse prostate compared to wildtype littermates (FIG. 12-D). Overexpression of ZIP1 significantly decreased the stearate mass isotopomer distribution from [5-$^{13}$C]glutamine indicating that ZIP1-mediated repression of aconitase hinders flow of carbon from glutamine to fatty acids (FIG. 19-D). These findings imply that SRC-2 stimulates aconitase enzyme activity in prostate cells at least in part by repressing ZIP1 expression to generate citrate-flux for lipogenesis (FIG. 12-E). Collectively, these data demonstrate that SRC-2-mediated usage of glutamine carbon via the reductive carboxylation pathway is a metabolic adaptation that prostate cancer cells, but not normal cells, have uniquely acquired to support lipogenesis.

Example 3

Glutamine Uptake Stimulates SRC-2 Function

Next the upstream signaling events were investigated that direct SRC-2 to promote glutamine-dependent lipogenesis. Recent studies identified glutamine as a potent signaling molecule (Duran, et al., 2012), especially in a nutrient-stressed environment such as a glucose-deprived state, stimulating nutrient uptake and energy metabolism (Nicklin, et al., 2009). On switching C4-2 cells from high-glucose/low-glutamine media to high-glutamine/low-glucose media, there was a moderate increase in expression of two SRC-2 target genes FASN and SCD which were subsequently hindered in SRC-2 depleted cells (FIGS. 4-A and 13-A). Quite unexpectedly, there was a robust increase in SRC-2 protein level (FIG. 4-A), and not mRNA (FIG. 13-A) in glutamine-rich culture conditions, suggesting a post-translational regulation of SRC-2 in glutamine stimulated prostate cancer cells.

Post-translational modifications such as phosphorylation have the potential to activate and increase the protein-turnover of the SRC-family of coactivators (Han, et al., 2009), and recent reports have identified PI3K-Akt and mTORC1, as potential kinases that are activated by nutrient uptake (Menendez, et al., 2007; Kamphorst, et al., 2013). Thus, SRC-2 protein expression was examined in glutamine-stimulated C4-2 cells treated with different kinase inhibitors targeting PI3K-Akt and mTORC1, and the effects to glucose-stimulated cells were compared. In a glutamine-stimulated condition, SRC-2 protein level was down-regulated by the mTORC1 inhibitor-Torin compared to DMSO-treated cells (FIG. 4-B), without any appreciable change in SRC-2 messenger expression (FIG. 13-B). However, this effect was not observed in a high glucose/low glutamine condition, and instead, the PI3K-inhibitor wortmannin (WORT) treatment showed some reduction in SRC-2 protein (FIG. 4-B). Surprisingly, rapamycin, a well-known inhibitor of mTORC1, failed to mimic the effects of Torin, indicating that SRC-2 may be one of the rapamycin-insensitive substrates of mTORC1 as postulated by others (Peterson, et al., 2011). Similarly, BEZ-235 a dual inhibitor of PI3K/mTORC1 failed to show any effect on SRC-2 protein stability in either culture conditions.

Increasing the concentration of glutamine treatment stimulates mTORC1 kinase activity (Duran, et al., 2012) as indicated by the phosphorylation of mTORC1-substrates S6K1 and 4E-BP1 (FIG. 13C), and immunoprecipitation of HA-SRC-2 from glutamine-treated C4-2 cells showed a dose-dependent increase in SRC-2-serine/threonine phosphorylation which was subsequently reversed by Torin treatment (FIG. 4-C). These data suggest that glutamine stimulation post-translationally modifies SRC-2 by phosphorylation, in an mTORC1-dependent manner. Next, the mechanism was investigated by which mTORC1-dependent phosphorylation on SRC-2 enhances SRC-2 protein levels. For this cycloheximide-protein degradation experiments were performed in C4-2 cells cultured in low glutamine (0.2 mM) or high glutamine (2.0 mM). Glutamine stimulation significantly increased SRC-2 protein stability and half-life as determined by cycloheximide-time dependent treatments (FIG. 14-A), but this increased SRC-2 protein stability was completely suppressed by mTORC1-inhibitor Torin (FIG. 14-B). These findings indicate that glutamine-mTORC1 dependent phosphorylation on SRC-2 confers stability of SRC-2 protein by increasing its half-life, thereby promoting increased levels of SRC-2 protein expression.

Finally, it was investigated whether mTORC1-inhibition affects the transcriptional activity of SRC-2. Glutamine signaling induced SRC-2 driven FASN-promoter activity (FIG. 4-D) as well as enhanced recruitment of SRC-2 to the FASN and SCD promoters (FIGS. 4-E and 4-F), and this glutamine dependent SRC-2 activity was significantly blocked by Torin (FIGS. 4-D, 4-E and 4-F). Taken together, these data demonstrate that glutamine uptake by tumor cells activates SRC-2 in a mTORC1 dependent manner (FIG. 4-G), which in turn, transcriptionally regulates expression of FASN and SCD thus promoting lipogenesis.

Example 4

SRC-2 Defines the Bioenergetics of Prostate Cancer Cells

To investigate whether SRC-2 expression defines the metabolic state of tumor cells, bioenergetic parameters were analyzed of prostate cancer cells upon perturbation of SRC-2. SRC-2-ablated C4-2 and PC-3 cells showed a significantly reduced basal metabolic rate (refer to 0-20 min time frame) compared to control non-targeting (shNT) cells (FIGS. 5-A and 15-A). While oligomycin treatment decreased the oxygen consumption (refer to 25-40 min time frame), addition of an uncoupler FCCP (Carbonyl cyanide 4-(trifluoromethoxy)phenylhydrazone) dramatically enhanced the oxygen consumption rate (OCR) indicating the maximal respiratory capacity (refer to 45-65 min time frame) in prostate cancer cells (FIGS. 5-A and 15-A). However, SRC-2-depleted cells showed a significantly reduced maximal metabolic rate compared to control (shNT) cells demonstrating its importance in the regulation of bioenergetics of prostate cancer cells (FIGS. 5-A and 15-A).

The metabolic rate of tumor cells cultured in different nutrient conditions was measured. Prostate cancer cells (shNT) exposed to high-glutamine/low-glucose exhibited both a higher basal (FIGS. 5-B and 15-B) and maximal metabolic rate (FIGS. 5-C and 15-C) compared to cells exposed to high-glucose/low-glutamine, indicating the importance of glutamine metabolism in the maintenance of a robust energetics program. In contrast, SRC-2 ablated cells exhibited a significantly lower basal (FIGS. 5-B and 15-B) and maximal metabolic rate (FIGS. 5-C and 15-C) with reduced proliferative rate compared to the control cells (FIGS. 5-E to 5-G). The maximal metabolic rate (FIG. 5-C) and proliferative capacity (FIGS. 5-F and 5-G) of SRC-2-depleted cells exposed to high-glutamine/low-glucose were similar to the control cells cultured in high-glucose/low-glutamine, suggesting that the loss of SRC-2 mimics a glutamine-deprived metabolic state. As expected, genetic inhibition of SRC-2 in prostate cancer cells led to a significantly reduced intracellular ATP pool, which exemplifies a metabolically-defective cellular state (FIG. 5-D). Colony formation assays mirrored similar effects, as SRC-2-depleted C4-2 and PC-3 cells showed poor survival (FIGS. 5-H and 5-I; FIGS. 15-D and 15-E). Taken together, these findings confirm that SRC-2 coordinates the metabolic functioning of tumor cells and promotes prostate cancer cell survival even under conditions of nutrient stress.

Example 5

SRC-2 is a Survival Factor for Prostate Cancer Metastasis

Tumor cell survival and proliferation are the major hallmarks of metastatic dissemination of cancer cells to distant sites (Hanahan & Weinberg, 2011). Given the importance of SRC-2 as the prime coordinator of energy metabolism balancing growth and survival, and its increased expression in metastatic prostate cancer patients (Taylor, et al., 2010), its role in promoting prostate cancer metastasis was investigated. Anchorage independent growth of tumor cells is a crucial step in the acquisition of malignancy, and silencing of SRC-2 significantly reduced the clonal-growth of both C4-2 and PC-3 cells in soft-agar (FIGS. 6-A and 6-B; FIGS. 16-A and 16-B). To determine whether SRC-2 expression promotes in vivo growth and survival of prostate cancer cells during the process of metastatic dissemination, a mouse model of experimental lung metastasis was utilized. SRC-2 ablated PC3-cells (sh18 and sh19) injected via tailvein in nude mice showed significantly reduced colonization and growth of the disseminated tumor cells in lungs five-weeks after injection compared to control-PC3 cells (shNT) (FIGS. 6-C and 6-D; FIG. 16-C).

Because loss of SRC-2 simulates a glutamine-deprived metabolic state with reduced growth and poor survival, it was considered whether reconstitution of SRC-2 (FIGS. 6-E and 16-D) or FASN expression in SRC-2-knockdown cells could rescue the phenotype. While forced overexpression of SRC-2 enhanced PC-3 (FIGS. 6-F and 6-G), and C4-2 growth and survival (FIGS. 16-E, 17-A and 17-B), re-expression of SRC-2 or its target gene FASN in SRC-2-depleted PC-3 cells rescued the survival-defects (FIGS. 6-F and 6-G), whereas a partial recovery was achieved in C4-2 cells (FIGS. 16-E, 17-A and 17-B). Reconstitution of SRC-2 also restored expression of its transcriptional targets FASN and SCD, confirming that SRC-2 is a prime-mediator of the lipogenic program in prostate tumorigenesis (FIG. 6-E).

Next, the opportunity to target the glutamine metabolic pathway in prostate cancer cells was exploited by using BPTES, a specific inhibitor of the glutaminase (GLS1) enzyme (Shukla, et al., 2012). Treatment of BPTES (1 µM) rapidly blocks the utilization of glutamine in cells (Shukla, et al., 2012; Jeong, et al., 2013), and there was a robust decrease in prostate cancer cell growth compared to DMSO (FIG. 6-H). SRC-2-depletion also attenuated growth of C4-2 and PC-3 cells similar to BPTES treated cells (1 µM), however at higher doses effect of BPTES on cell growth was stronger than SRC-2-ablation. These findings suggest that targeting the SRC-2 or glutamine metabolic pathway may be beneficial for prostate cancer therapy.

Finally, to confirm that SRC-2 inhibition blocks prostate tumor growth and metastasis, SRC-2-depleted PC-3 cells (sh19) were surgically implanted orthotopically into the mouse prostate, and the primary tumor growth and metastasis with the control cells (shNT) eight weeks post-surgery was compared. While mice harboring transplanted shNT-PC-3 cells showed robust growth of primary prostate tumors (FIGS. 7-A and 7-B; FIGS. 17-C, 17-D, 17-E) and large numbers of metastatic lesions (FIGS. 7-A and 7-C; FIG. 17-C), SRC-2 depleted PC-3 cells developed smaller primary tumors (FIGS. 7-A and 7-B) and a dramatically reduced number of metastatic lesions were observed (FIGS. 7-A and 7-C). Gene expression profiling confirmed significantly lower FASN and SCD in SRC-2 depleted orthotopic tumors compared to shNT-PC-3 tumors (FIG. 17-D). Next, the levels of key metabolites in the mouse orthotopic prostate tumors were profiled using mass spectrometry that revealed significantly reduced amounts of glutamate and fatty acids such as palmitic acid and oleic acid, and low levels of palmitoleic acid in SRC-2-ablated tumors (FIGS. 7-D to 7-G). These findings demonstrate that SRC-2 regulated metabolic reprogramming is a critical determinant of prostate cancer cell survival and this mechanism may select variant clones for aggressive metastasis. The findings substantiate the dominant role of SRC-2 in prostate cancer growth and metastasis, and indicate that inhibition of SRC-2 is beneficial for treating metastatic prostate cancer.

In order to obtain clinical insights, expression of SRC-2, FASN and SCD were examined in a patient-derived RNA-seq dataset containing tissue-samples (n=132) collected from benign adjacent (benign) (n=16), organ confined prostate cancer (PCA) (n=68) and metastatic prostate cancer (mets) (n=48). Importantly, enhanced expression of SRC-2 was observed in prostate cancer patients particularly in metastatic patients (FIG. 7-H), with a concomitant increase in the expression of its transcriptional targets FASN and SCD (FIGS. 7-I and 7-J). In the context of these findings, a metabolomic profiling dataset which was a subset of the larger RNAseq cohort (Sreekumar, et al., 2009) described above was re-analyzed. The metabolomic data set contained tissues from benign adjacent prostate (n=16), organ confined prostate cancer (n=12, PCA) and metastatic prostate cancer (n=14, Mets). Glutamate levels were significantly increased on disease progression from benign to PCA to metastatic prostate cancer (FIG. 7-K), while a decreasing trend was noted for glucose levels (FIG. 17-F). Fatty acids such as oleic acid (FIG. 7-L) and palmitoleic acid (FIG. 17-G) on the other hand were increased in metastatic prostate cancer. These data support the findings that the glutamine-dependent lipogenic program is enhanced in metastatic prostate tumors, and that overexpressed-SRC-2 is one of the prime regulators of this metabolic reprogramming. These clinical observations substantiate the findings that elevated levels of SRC-2 promote prostate cancer metastasis by imparting metabolic advantages to the tumor cells, thus licensing for an uncontrolled growth and metastasis.

Example 6

Exemplary Methods and Material

Cell Culture—
LNCaP, C4-2 and PC-3 cells were cultured in RPMI (Invitrogen, CA) supplemented with 10% fetal bovine serum (FBS, Invitrogen, CA) and penicillin/streptomycin (PS) (Invitrogen, CA). HeLa cells were cultured in DMEM (Invitrogen, CA) with 10% FBS and 1% PS. For nutrient-stressed experiments following media compositions were used. High glucose/low glutamine: RPMI[−] Glutamine (Cat#21870, Invitrogen, CA) supplemented with 0.2 mM L-Glutamine (Invitrogen, CA), final concentration of D-glucose (11 mM), 10% dialyzed FBS and 1% PS. Low glucose/high glutamine: RPMI[−]Glucose (Cat#11879, Invitrogen, CA) final L-glutamine concentration 2.0 mM, supplemented with D-glucose 5 mM, 10% dialyzed FBS and 1% PS.

Reagents and Plasmids—
Kinase inhibitors were obtained from following sources: Rapamycin (Calbiochem), Torin1 (Tocris), BEZ235 (Selleck Chemicals) and Wortamanin (Sigma). Following antibodies were used: SRC-2 (BD Biosciences and Bethyl Laboratories), SCD (Abcam), FASN, mTORC1-sampler kit, HA-tag (Cell Signaling), phospho-Serine/Threonine (BD Biosciences). Plasmids used are: pCR3.1-SRC-2, pcDNA3.1-flag-SREBP-1a (Addgene), pGL3-Zip1, Fasn-luc (Addgene) and SCD-luc (Switchgears genomics).

Animals—
All animal experiments were performed in accordance with the Animal Care Research Committee at Baylor College of Medicine. The generation of the SRC-2−/− mice has been described previously (Gehin, et al., 2002), and age-matched male littermate mice were used. For tumor studies, male athymic nude mice of 6-7 weeks (Harlan) were used for experimental lung metastasis assay and male FOX Chase SCID mice of 6-7 weeks (Charles River Laboratories) for orthotopic xenograft experiments.

Lentiviral-Mediated Generation of Cells with Knockdown of SRC-2—
Stable cells with decreased expression of SRC-2 were generated by lentiviral-mediated shRNA expression. pGIPZ vector expressing shRNA sequences targeting SRC-2 (two clones: #186064 and #199063) or non-targeting (control: shNT) were obtained (OpenBiosystems, PA) and virus were generated at CBASS-BCM core facility. Polyclonal pooled populations of stable cells were selected in presence of puromycin (1 µg/mL) for more than three passages before initiating any functional or tracer experiments.

Luciferase Assay—
Luciferase assays were performed using Luciferase Reporter Assay (Promega) and a Berthold 96 well plate reader. Luciferase values were normalized to the total protein level.

Chromatin Immunoprecipitation (ChIP)—
ChIP assays were performed according to an EZ ChIP kit (Millipore) with some modification. Briefly, C4-2 stable cells were grown in 15 cm dishes until 80% confluent and stimulated with glutamine with/without Torin (250 nM), followed by chromatin shearing and qPCR.

Metabolomic Profiling—
Metabolomic analyses were performed as described elsewhere (Putluri, et al., 2011). Briefly, cell pellets and tumor tissues were stored at −140° C. until analysis. For extraction of metabolome, 5×10$^6$ C4-2 cells treated with either siRNA-GFP (control) or siRNA-SRC-2 with three replicates each and for tissues 10 mg of tumor were homogenized in 1:4 ice cold water:methanol mixture containing an equimolar mixture of isotopic labeled compounds: Jasmonic acid, [15N] 2Tryptophan, and [15N] Anthranilic acid. For tumor tissues, 10 mg of This was followed by sequential addition of ice cold chloroform and water in 3:1 ratio and separation of the organic (methanol and chloroform) and aqueous solvents (water:methanol:chloroform:water; ratio 1:4:3:1). The aqueous extract was de-proteinized using a 3 KDa molecular filter (Amicon Ultracel—3K Membrane, Millipore Corporation, Billerica, Mass.) and the filtrate containing metabolites was dried under vacuum (Genevac EZ-2plus, Gardiner, N.Y.). Prior to mass spectrometry, the dried extract was resuspended in an identical volume of injection solvent composed with appropriate mobile phase and subjected to liquid chromatography (LC) mass spectrometry. The chromatographic separation of metabolites was performed using either reverse phase (RP) separation with QQQ mass spectrometers (Agilent Technologies, Santa Clara, Calif.). Targeting the metabolites, the normal phase chromatographic separation was also used for targeted identification of metabolites.

Isotope Labeling and Profiling by Targeted Mass Spectrometry—
Nutrients-labeled with $^{13}C$ were purchased from Cambridge Isotope Laboratories, MA. C4-2 cells were grown in six-well plates in regular media until 80% confluent, followed by addition of 2.0 mM of L[U-$^{13}C_5$]glutamine supplemented in RPMI[−] Glutamine with 10% dialyzed FBS and 1% PS; or 11 mM D[U-$^{13}C_6$]glucose supplemented in RPMI[−]Glucose, 10% dialyzed FBS and 1% PS. Cell were grown until 80% confluent, followed by addition of $^{13}C$ containing media for zero, six and twelve hours. At the indicated time-points, culture medium was collected, cells washed with PBS, and equal number of cells were snap-frozen using liquid nitrogen. Ten microliters were injected and analyzed using a 6490 QQQ triple quadrupole mass spectrometer (Agilent technologies) coupled to a 1290 series HPLC system via selected reaction monitoring (SRM). SRMs were created for expected $^{13}C$ incorporation in various forms for targeted LCMS/MS. To assess the validity of the method for calculating isotopomers, the complete isotopomer distributions for each metabolite was determined. Data analysis was performed in Quantitative analysis and estimated the % of isotopomer incorporation using the formula [% of Incorporation=$^{13}C/^{13}C+^{12}C)\times 100$] and subtracted with the natural abundance. Values were normalized to the cell number.

Enzyme Activities—
Isocitrate dehydrogenase (IDH) (Cat#MAK062), citrate synthase (CS) (Cat#CS0720) and aconitase (ACO)

(Cat#MAK051) enzyme activities were measured using the kits from Sigma, according to manufacturer's protocol. Briefly, cells were seeded in 15 cm dishes until 80% confluent. Cells were lysed in ice-cold conditions using the lysis buffer provided in the kit supplemented with protease and phosphatase inhibitor cocktail (Millipore). Equal amounts of protein were used for the enzyme activity assay.

RNA-Seq of Tumor Samples—

The RNA-Seq cohort was comprised of 132 prostate tissues sequenced at MCTP (Michigan Center for Translational Pathology). Sequencing data were aligned using TopHat 2.0.8 against the Ensembl 69 GRCh37 human genome build and FPKM was calculated across genes in Ensembl 69 using Cufflinks 2.0.2. Graphs were created using a variety of custom R and python scripts.

Metabolomic Data Analysis—

The normalized data was taken from the publication of (Sreekumar et al., 2009). A permutation based P-value (10000 permutation of sample labels) was performed to define the significance of metabolites in different categories. The data was further plotted using boxplot in R language.

Oil Red-O Staining—

Cells were grown on coverslips placed in a six-well plate until 80% confluent. Cell culture medium were aspirated and cells were washed with PBS, and then fixed by adding 2 mL of 10% formalin for 30 minutes, followed by 60% isopropanol for 5 minutes. Oil Red O stock solution was then diluted and filtered according to manufacturer's protocol (Cayman Chemicals, MI), and finally added to stain the cells for 5 minutes. Cells were washed, dried and coverslips were mounted on slides using prolong gold anti-fade DAPI (Invitrogen, CA). Slides were imaged using Olympus microscope.

Additional Metabolomic Profiling—

Reagents and internal standards: High-performance liquid chromatography (HPLC) grade acetonitrile, methanol and water were purchased from Burdick & Jackson, NJ. Mass spectrometry grade formic acid and internal standards namely, [15N]2Tryptophan, and [15N] Anthranilic acid were purchased from Sigma-Aldrich, MO. The calibration solution containing multiple calibrants in acetonitrile/trifluroacetic acid/water was purchased from Agilent Technologies, CA. The metabolomics analyses of all samples were executed using the protocol described previously. The raw data (LC-MS output) was normalized using internal standards (Putluri, Shojaie, et al, 2011).

Liquid Chromatography/Mass Spectrometry (LC/MS):

The chromatographic separation of metabolites was performed using either reverse phase (RP) separation or normal phase online with QQQ mass spectrometers (Agilent Technologies, Santa Clara, Calif.).

Separation of Metabolites (Palmitoleic Acid and Oleic Acid):

Targeting the metabolites, the normal phase chromatographic separation was also used for targeted identification of metabolites (Putluri, Shojaie, et al, 2011). This employed solvents containing water (solvent A), with solvent A modified by the addition of 5 mM Ammonium acetate (pH 9.9), and 100% acetonitrile (ACN) solvent B). The binary pump flow rate was 0.2 ml/min with a gradient spanning 80% B to 2% B over a 20 minute period followed by 2% B to 80% B for a 5 min period and followed by 80% B for 13 minute time period. The flow rate was gradually increased during the separation from 0.2 mL/min (0-20 mins), 0.3 mL/min (20.1-25 min), 0.35 mL/min (25-30 min), 0.4 mL/min (30-37.99 min) and finally set at 0.2 mL/min (5 min). Metabolites were separated on a Luna Amino (NH2) column (4 um, 100 A 2.1×150 mm, Phenominex), that was maintained in a temperature controlled chamber (37° C.). All the columns used in this study were washed and reconditioned after every 50 injections.

Sample Preparation for Mass Spectrometry-Based Examination of Metabolome from Orthotopic Mouse Tumors:

Orthotopic mouse tissues were stored at −140° C. in liquid nitrogen until analysis. For extraction of metabolome, 10 mg of tissue was homogenized in 1:4 ice cold water:methanol mixture containing a [15N]2Tryptophan. This was followed by sequential addition of ice cold chloroform and water in 3:1 ratio and separation of the organic (methanol and chloroform) and aqueous solvents (water:methanol:chloroform: water; ratio 1:4:3:1). The aqueous extract was de-proteinized using a 3 kDa molecular filter (Amicon Ultracel-3K Membrane, Millipore Corporation, MA) and the filtrate containing metabolites were dried under vacuum (Genevac EZ-2plus, NY). Prior to mass spectrometry, the dried extract was resuspended in an identical volume of injection solvent composed with appropriate mobile phase and subjected to liquid chromatography (LC) mass spectrometry.

Separation of Metabolites:

Reverse phase chromatographic separation was used for targeted identification of metabolites. For this solvents containing water (solvent A), solvent A modified by addition of 10 mM Ammonium acetate, and 100% Methanol (MeOH) as solvent B were employed. Gradient: 40% B to 100% B over a 23 minute time period. Flow rate: 0.2 ml/min. Metabolites were separated on a Luna Phenyl Hexyl column (3 um, 2×150 mm, Phenominex), that was maintained in a temperature controlled chamber (400° C.).

Additional Isotope Labeling and Profiling by Targeted Mass Spectrometry—

Nutrients-labeled with $^{13}$C were purchased from Cambridge Isotope Laboratories, MA. C4-2 cells were grown in six-well plates in regular media until 80% confluent, followed by a overnight starvation and then addition of 2.0 mM of L[U-$^{13}$C$_5$]glutamine supplemented in RPMI[−] Glutamine with 10% dialyzed FBS and 1% PS; or 11 mM D[U-$^{13}$C$_6$]glucose supplemented in RPMI[−]Glucose, 10% dialyzed FBS and 1% PS. At the indicated time-points, culture medium was collected, cells washed with PBS and equal number of cells from each treatment were snap-frozen using liquid nitrogen. Cells were scrapped in 0.5 ml of 1:1 mixture of water:methanol, sonicated for 1 min (30 sec pulse twice) and then mixed with 450 µl of ice cold chloroform. The resulting homogenate was then mixed with 150 µl of ice cold water and vortexed again for 2 min. The homogenate was incubated at −20° C. for 20 min and centrifuged at 4° C. for 10 min to partition the aqueous and organic layers. The aqueous and organic layers were combined and dried at 37° C. for 45 min in an automatic Environmental Speed Vac® system (Thermo Fisher Scientific, IL). The extract was reconstituted in 500 µl of ice cold methanol:water (1:1) and filtered through 3 KDa molecular filter (Amicon Ultracel-3K Membrane, Millipore Corporation, MA) at 4° C. for 90 min to remove proteins. The filtrate was dried at 37° C. for 45 min in speed vac and stored at −80° C. until mass spectrometry analysis. Prior to mass spectrometry analysis, the dried extract was resuspended in 50 µL of methanol:water (1:1) containing 0.1% formic acid and then analyzed using MRM. Ten microliters were injected and analyzed using a 6490 QQQ triple quadrupole mass spectrometer (Agilent technologies) coupled to a 1290 series HPLC system via selected reaction monitoring (SRM). Metabolites were targeted in both positive and negative ion mode, ESI voltage was +4000 V in positive ion mode and −3500 V in negative ion mode. Approximately 9-12 data points were acquired per detected metabolite. Samples were delivered to the MS via normal phase chromatography using a Luna Amino column (4 um, 100 A 2.1×150 mm, Phenominex) at 400 ml/min gradient spanning 80% B to 2% B over a 20 minute period followed by 2% B to 80% B for a 5 min period and followed by 80% B for 8 minute time period re-equilibrate the column. Buffer A was comprised of 5 mM ammonium acetate (pH=9.9) in water:acetonitrile. For $^{13}C$ labeled experiments, SRMs were created for expected $^{13}C$ incorporation in various forms for targeted LC-MS/MS. To assess the validity of the method for calculating isotopomers, the complete isotopomer distributions for each metabolite was determined. Data analysis was performed in Quantitative analysis and estimated the % of isotopomer incorporation using the formula [% of Incorporation=$^{13}C/^{13}C+12C$)×100] and subtracted with the natural abundance.

Oxygen Consumption—

The oxygen consumption rate (OCR) was measured using a Seahorse Bioscience XF24 Extracellular Flux Analyzer according to manufacturer's protocol. Briefly, cells were seeded in triplicates at equal densities (25,000 cells per well) into XF24 tissue culture plates. For nutrient stressed conditions, cell media was changed 12 hr after cell seeding into high glucose/low glutamine or low glucose/high glutamine. Oxygen consumption was measured under basal conditions (DMSO), oligomycin and mitochondrial uncoupler trifluoromethoxy carbonyl cyanide phenyl 59ydrazine (FCCP) (2 mM) using the mito-stress kit (Seahorse Bioscience). Oxygen consumption values were normalized to cell number.

siRNA and Adenovirus— siRNAs targeting SRC-2, SREBP-1, and GFP were obtained from Invitrogen and Dharmacon and Lipofectamine 2000 (Invitrogen, CA) was used for transfection. SRC-2 siRNAs used are: siSRC-2 (#1: HSS116116; #2: HSS116117) from Invitrogen; and siSRC-2 (L-020159SREBF1 (L-006891) from Dharmacon; siS-REBF1 (L-006891) from Dharmacon; and control GFP-siRNA (12935-145) from Invitrogen and non-targeting siRNA (D-001810) from Dharmacon. Adenovirus expressing full-length human SRC-2 and GFP were cloned in pAdeno-X (Clonetech) plasmid and virus was amplified and purified at Gene Vector Core Laboratory, BCM. Purified virus was then used to infect human prostate cancer cells. Adenovirus expressing FASN was obtained from Signagen (Catalog #: SL100773).

Measurement of Glucose, Glutamine and ATP Levels—

Glucose and glutamine consumption were measured in LNCaP, C4-2 and PC-3 cells transfected with siRNAs targeting GFP or SRC-2, using Biovision Kits (Cat# K606-100 and K629-100), according to manufacturer's instructions. Briefly, cells were starved overnight in low glucose/low glutamine medium (0.2 mM L-Glutamine and 5 mM D-Glucose) followed by incubation in complete media containing 11 mM D-Glucose and 2 mM-L-Glutamine. Cells were harvested at each hour timepoints for 6 hours, followed by colometric estimation of cell lysates and spent media. Data collected was then background corrected from time (t=0) and the amount of metabolite consumed was calculated per hour normalized to total protein. ATP levels in the cell were measured using StayBrite Highly Stable ATP assay (Biovisoin). Briefly, cells lysates were mixed in reaction buffer, and luminescent readings were acquired using Berthold 96 well plate reader. ATP levels were calculated based on a standard curve of known ATP concentrations and data generated was normalized to total protein concentration.

Luciferase Assay—

Luciferase promoter constructs were obtained from following sources: FASN-Addgene, SCD-Switchgear genomics and ZIP1—Peter Makhov (Fox Chase Cancer Center). FASN-luc (25 ng or 75 ng), SCD-luc (100 ng or 500 ng) and ZIP1-luc (100 ng or 500 ng) promoter constructs were transfected into HeLa cells or PC-3 cells, respectively seeded in twenty-four well plates at the indicated concentrations along with SREBP-1 (20 ng/well) and SRC-2 (50 ng/well). Control lanes were transfected with empty vector and the total amount of DNA in each well were normalized by adding blank-plasmids. Cells were harvested two days after transfection and luciferase assay performed using a Luciferase Reporter Assay (Promega) and a Berthold 96 well plate reader. Luciferase values were normalized to the total protein level.

Gene Expression Analyses—

Total mRNA was isolated from prostate cancer cells, tissues and tumors using the RNeasy Kit (QIAGEN). Reverse transcription was carried out using Superscript VILO cDNA synthesis kit (Invitrogen, CA) according to the manufacturer's instructions. For gene expression analysis, qPCR was performed using the Taqman system (Roche) with sequence-specific primers and the Universal Probe Library (Roche). Actin was used as an internal control. Melting curve analysis was performed to ensure that a single PCR product expected was produced in a given well. Three biological replicates for each treatment group were used. Data was analyzed using the comparative Ct method (ΔΔCt). In addition, a human fatty acid metabolism PCR array Cat#PAHS-007Z (SA Biosciences, CA) was used to measure 84 key genes involved in the regulation and enzymatic pathways of fatty acid metabolism using SYBER green (QIAGEN), according to the manufacturer's instructions. Data obtained was analyzed using RT$^2$ Profiler™ PCR Array Data Analysis software (SA Bioscineces, CA). Primer sequences are available on request.

Cell Growth and Clonogenic Survival Assays—

Cells were seeded in 96-well plates in complete medium, and after the cells attached to the bottom surface they were incubated in nutrient-stressed medium. The cell growth was measured using Cellglo kit (Promega) according to manufacturer's instructions. For the clonogenic survival assays, 200 cells per well were plated onto a 6-well plate, and were incubated in nutrient-stressed medium for 14 days, and stained with crystal violet. For the rescue experiment respective adenovirus were added in the medium. The medium was changed every two days.

Soft-Agar Colony Formation Assay—

The assay was performed with C4-2 and PC-3 stable cells using a cell transformation detection assay kit (Millipore), according to manufacturer's protocol. Briefly, 1500 cells/well were mixed with 0.4% top agar solution and layered on top of 0.8% agar base layer, and finally covered with complete growth medium. The colonies formed were detected by addition of cell stain solution after 10 days and were imaged by UVP-Biospectrum.

Cycloheximide Protein Stability Assays—

SRC-2 protein stability was studied by cycloheximide treatment experiments in C4-2 cells for different time points as described previously (Li C, Jo A, et al, 2011). C4-2 cells were cultured in low glutamine (0.2 mM) or high glutamine (2.0 mM) followed by treatment with cycloheximide (0.5 mM). For Torin treatment, C4-2 cells cultured in high glutamine were either treated with DMSO (vehicle-control) or Torin (250 nM) prior to cyclohexamide treatments. Cells were lysed followed by Western immunoblotting.

Chromatin Immunoprecipitation (ChIP)—

The following antibodies were used for ChIP: SRC-2 (Bethyl Laboratories), SREBP-1 (Santacruz), rabbit IgG, and mouse IgG. ChIP assays were performed according to an EZ ChIP kit (Millipore) with some modification (Foulds, Feng, et al., 2013). Briefly, C4-2 stable cells were grown in 15 cm dishes until 80% confluent. For glutamine stimulation, cells were glutamine-deprived overnight by incubating in low glutamine medium (0.2 mM L-Glutamine and 11 mM D-Glucose), followed by 4 hours pre-treatment with or without Torin (250 nM), a mTORC1 selective inhibitor, and with/without high glutamine (2 mM L-glutamine and 11 mM D-glucose) treatment for one hour, before crosslinking in 1% formaldehyde and quenching with glycine. Chromatin was sheared by sonication using a Sonifier, precleared with control IgG antibodies and agarose beads (Millipore), and then immunoprecipitated with IgG (control), SRC-2 and SREBP-1 antibodies. DNA fragments were eluted from beads followed by reverse-crosslinking and purified DNA was used in qPCR reactions using SYBR green to determine the promoter occupancy.

Androgen and SRC3 Response Gene Signatures—

The androgen response gene signatures were derived as previously described (Wang Q, Li W, et al., 2007). The LNCaP siAR gene signature was derived after treating LNCaP cells in full media with siAR (Invitrogen) for 72 hours. The siSRC2 gene signature was derived after treating LNCaP cells in full media with siSRC2 (Invitrogen) for 48 hours. Gene expression profiling was carried out utilizing the Affymetrix Human Exon 1.0 ST Array platform at the Genomic and RNA Profiling Core (G.A.R.P.) at Baylor College of Medicine. Gene expression differences were inferred utilizing the t-test (p<0.05) and imposing a fold change exceeding 4/3×, using the R statistical system.

Gene Set Enrichment Analysis—

Gene set enrichment analysis was carried out using the GSEA software package (Subramanian A, Tamayo P, et al, 2005). Normalized Enrichment Score (NES) and adjusted q-valued were computed utilizing the GSEA method, based on 1000 random permutations of the ranked genes.

Experimental Lung Metastasis—

PC-3 stable cells expressing control shNT, SRC-2 sh18, and sh19 were trypsinized, washed with PBS, and finally resuspended in PBS ($5 \times 10^6$ cells/mL). Two hundred μl of the cell suspension ($1 \times 10^6$ cells/mL) was injected via tail-vein into each Nude male mouse (Harlan Laboratories) at the age of 6 to 7 weeks (n=7). Mice were sacrificed 5 weeks after injection and lungs were perfused with PBS and excised. Part of the lung was fixed in 4% paraformaldehyde, embedded in paraffin, and sectioned at a thickness of 4 μM for histological examination by H&E staining.

Prostate Cancer Orthotopic Mouse Model—

PC-3 stable cells expressing control shNT and SRC-2-sh19 (GFP-labeled) were injected orthotopically into the prostates of 8- to 10-week-old nude mice (n=5), using $1 \times 10^6$ cells in a volume of 20 μL (Yu, Feng, et al, 2011). Mice were sacrificed at 10 weeks after injection, and the primary tumor foci and metastatic lesions were analyzed by GFP-imaging. The primary tumor volume was calculated using [ab2×0.5, where a>b] using slide calipers and the number of GFP-positive metastatic lesions were also counted.

Cell Culture Treatment Conditions, Protein Isolation and Western Blotting—

For, siRNA treatments cells were lysed 72 hours post-transfection. Stable cells were grown till 80% confluency before protein was extracted. During nutritional stress conditions, stable cells were cultured in complete media till 80% confluency, followed by an overnight starvation in low glucose/low glutamine medium (0.2 mM L-Glutamine and 5 mM D-Glucose). Cells were then switched to high glucose (11 mM)/low glutamine (0.2 mM) medium, or high glutamine (2 mM)/low glucose (5 mM) medium, as indicated in the figures, for 24 hours before cells were lysed. For kinase inhibitor treatments, cells were incubated in indicated medium along with inhibitors for 12 hours before cells were harvested and lysed. Western blot was performed as described previously (York, Reineke, et al., 2012). Briefly, cells were lysed using NP-40 lysis buffer (Invitrogen, CA) along with protease and phosphatase inhibitor cocktail (Millipore, CA). Total protein was estimated using BCA-protein estimation kit (Pierce, IL) and approximately 40 μg of proteins were separated by 4-12% Bis-Tris gels (Invitrogen, CA) and electroblotted onto nitrocellulose membranes using the iBlot system (Invitrogen, CA). Blots were blocked for 2 hour at room temperature or overnight at 4° C. in 1×TBS buffer (Biorad, CA) supplemented with 0.1% Tween-20 (Sigma, MO) supplemented with 5% bovine serum albumin (BSA) or 5% non-fat dry milk (Biorad, CA). Blots were incubated overnight at 4° C. with primary antibody diluted into TBST containing 1% BSA or 5% non-fat dry milk. Blots were subsequently washed three times for 10 mins in TBST and incubated with secondary antibody coupled to horse-radish peroxidase (Promega, WI). Blots were washed as previously described, reacted with ECL reagents (Thermo Scientific) and detected by chemi-luminescence (UVP Biospectrum, CA).

Immunoprecipitations—

C4-2 cells were cultured in five 100 mm dishes until 80% confluency, followed by infection with Adv. GFP (one plate) or Adv. SRC-2 (expressing HA-tagged SRC-2) in four plates. Twenty four hours post-infection media was changed and cells were incubated overnight in low glutamine medium (0.2 mM L-Glutamine and 11 mM D-Glucose, and 10% dialyzed-FBS). C4-2 cells expressing Adv. SRC-2 were pre-treated for 4 hours with either DMSO or Torin (250 nM), a mTORC1 selective inhibitor and then stimulated with different concentrations of L-Glutamine (0.2 mM, 2 mM, and 4 mM) supplemented with 11 mM D-glucose and 10% dialyzed serum as indicated in the figure for one hour. Cells were lysed in NP-40 lysis buffer (Invitrogen, CA) supplemented with protease and phosphatase inhibitor cocktail (Millipore, CA) and precleared with control Protein A/G Agarose beads (Pierce, IL). Five hundred micrograms of protein were then used for pulldown assays using monoclonal anti-HA-agarose antibody beads (Sigma, MO) overnight. The beads were then captured, washed and immunoprecipitated proteins were eluted and subjected to western blotting, along with 2% input sample.

Immunohistochemistry—

Immunohistochemistry was performed as described previously (Han, Hawkins, et al, 2012). Mouse monoclonal anti-human Ki-67 antibody MIB-1 (Dako, Denmark) was used to stain the lungs sections followed by anti-mouse Alexa-594 secondary antibody (Molecular Probes, CA).

Statistical Analyses—

Unless otherwise mentioned all results are shown as the mean±standard error mean (s.e.m.) and standard statistical comparison of different groups were carried out using two-tailed unpaired Student's t test. For all statistical analyses, differences of p<0.05 were considered statistically significant, and experiments were repeated at least three times. Graphpad software version 4.0 was used for data analysis.

REFERENCES

Agoulnik, et al., *Cancer Res.* 66:10594-10602, 2006.
Cantor & Sabatini, *Cancer. Discov.* 2:881-898, 2012.

Chopra, et al., *Cell. Metab.* 13:35-43, 2011.
Chopra, et al., *Science* 322:1395-1399, 2008.
Costello, et al., *J. Biol. Chem.* 272:28875-28881, 1997.
Csibi, et al., *Cell* 153:840-854, 2013.
Currie, et al., *Cell. Metab.* 18:153-161, 2013.
Dasgupta, et al., *Annu. Rev. Med.* 65:279-92, 2014.
Dasgupta, et al., *J. Carcinog.* 11:4, 2012.
DeBerardinis, et al., *Proc. Natl. Acad. Sci. U.S.A* 104:19345-19350, 2007.
Duran, et al., *Mol. Cell* 47:349-358, 2012.
Duteil, et al., *Cell. Metab.* 12:496-508, 2010.
Fendt, et al., *Cancer Res.* 73:4429-4438, 2013.
Foulds, et al., *Mol. Cell.* 2:185-199, 2013.
Gameiro, et al., *Cell. Metab.* 17:372-385, 2013.
Gao, et al., *Nature* 458:762-765, 2009.
Gehin, et al., *Mol. Cell. Biol.* 22:5923-5937, 2002.
Han, et al., *Nat. Med.* 7:1102-1111, 2012.
Han, et al., *Trends Endocrinol. Metab.* 20:8-15, 2009.
Hanahan & Weinberg, *Cell.* 144:646-674, 2011.
Igal, *Carcinogenesis* 31:1509-1515, 2010.
Jeong, et al., *Cancer. Cell.* 23:450-463, 2013.
Kamphorst, et al., *Proc. Natl. Acad. Sci. U.S.A* 110:8882-8887, 2013.
Kim, et al., *J. Clin. Invest.* 101:1-9, 1998.
Koochekpour, et al., *Clin. Cancer Res.* 18:5888-5901, 2012.
Kosaka, et al., *Sci. Rep.* 3:1268, 2013.
Li, et al., *Oncogene.* 30(42):4350-64, 2011.
Liu, et al., *Prostate* 60:98-108, 2004.
Menendez & Lupu, *Nat. Rev. Cancer.* 7:763-777, 2007.
Metallo, et al., *Nature* 481:380-384, 2011.
Mullen, et al., *Nature* 481:385-388, 2011.
Nicklin, et al., *Cell* 136:521-534, 2009.
Peterson, et al., *Cell* 146:408-420, 2011.
Picard, et al., *Cell* 111:931-941. 2002.
Price, et al., *J. Urol.* 168:273-280, 2002.
Putluri, et al., *PLoS One* 6:e21417, 2011.
Putluri, et al., *PLoS One.* 7:e21417, 2011.
Rossi, et al., *Mol. Cancer. Res.* 1:707-715, 2003.
Seo, et al., *Proc. Natl. Acad. Sci. U.S.A* 106:13765-13769, 2009.
Shukla, et al., *J. Med. Chem.* 55:10551-10563, 2012.
Singh, et al., *Mol. Cancer.* 5:14, 2006.
Singh, et al., *Mol. Cancer.* 5:14, 2006.
Smolkova, et al., *Int. J. Cell. Biol.* 2012:273947, 2012.
Sreekumar, et al., *Nature* 457:910-914, 2009.
Sreekumar, et al., *Nature.* 7231:910-914, 2009.
Subramanian, et al., *PNAS USA.* 102(43):15545-50, 2005.
Taylor, et al., *Cancer. Cell.* 18:11-22, 2010.
Vander Heiden, et al., *Science* 324:1029-1033, 2009.
Wang, et al., *Molecular Cell.* 27(3):380-92, 2007.
Wang et al., *Cancer Res.* 74(5):1506-17, 2014
Ward & Thompson, *Cancer. Cell.* 21:297-308, 2012.
Wise, et al., *Proc. Natl. Acad. Sci. U.S.A* 105:18782-18787, 2008.
Yoo, et al., *J. Biol. Chem.* 283:20621-20627, 2008.
York, et al., *Cell. Metab.* 5:752-763, 2012.
Yu, et al., *Clin. Cancer Res.* 13:4355-4366, 2011.
Zadra, et al., *Biochim. Biophys. Acta* 1831:1518-1532, 2013.
Zhang, et al., *Methods Enzymol.* 542:369-389, 2014.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method of treating an individual for metastatic prostate cancer, or preventing or reducing metastatic cancer in the individual, comprising the step of providing a therapeutically effective amount of treatment for the metastatic prostate cancer when a sample from the individual indicates that there is an elevated level of SRC-2 in cells from the sample, wherein the level is measured by the following:
   administering $^{13}C$-labeled glutamine to the individual;
   obtaining a sample from the individual, wherein the sample is suspected of comprising or known to comprise cancer cells; and one of the following:
   1) measuring the level of citrate m+5 or the ratio of citrate m+5/citrate m+4 from the cells after the administering step, wherein when the level of citrate m+5 or the ratio is elevated compared to a reference level measured before administration, the individual is in need of treatment, prevention, or the reduction of metastatic cancer, or
   2) measuring after the administering step for the presence of $^{13}C$ in one or more of palmitic acid, stearic acid, palmitoleic acid, oleic acid, and myristic acid, wherein when $^{13}C$ is present, the individual is in need of treatment, prevention, or the reduction of metastatic cancer, or
   3) measuring the level of citrate m+1 from the cells after the administering step, wherein when the level of citrate m+1 is elevated compared to a reference level measured before administration, the individual is in need of treatment, prevention, or the reduction of metastatic prostate cancer.

2. The method of claim 1, wherein the sample is urine, serum, blood, tissue biopsy, prostatic fluid, semen, breath, secretions, or a mixture thereof.

3. The method of claim 1, wherein the treatment comprises one or more agents that inhibit the level and/or activity of SRC-2.

4. The method of claim 3, wherein the agents comprise one or more functionally active derivatives of bufalin.

5. The method of claim 1, wherein the treatment comprises chemotherapy, hormone therapy, immunotherapy, radiation, surgery, or a combination thereof.

6. The method of claim 1, further comprising the step of administering one or more glutamine analogs to the individual.

7. The method of claim 6, wherein the one or more glutamine analogs is selected from the group consisting of 6-diazo-5-oxo-L-norleucine (DON), L-g-glutamyl-p-nitroanilide (GPNA), and a mixture thereof.

8. The method of claim 1, wherein the treatment comprises a LHRH analog, antiandrogen, or a combination thereof.

9. The method of claim 8 wherein the LHRH analog is leuprolide, goserelin, triptorelin, histrelin, or a combination thereof.

10. The method of claim 8 wherein the antiandrogen is flutamide, bicalutamide, nilutamide, or a combination thereof.

11. The method of claim 1, wherein the treatment comprises abiraterone, MDV3100, Ipilimumab, bisphosphonate, leuprolide, or a combination thereof.

12. The method of claim 1 wherein citrate m+5 is measured after administration of [U-$^{13}$C]glutamine.

13. The method of claim 1 wherein citrate m+1 is measured after administration of [1-$^{13}$C]glutamine.

* * * * *